(12) United States Patent
Kurkjian et al.

(10) Patent No.: US 7,025,138 B2
(45) Date of Patent: Apr. 11, 2006

(54) METHOD AND APPARATUS FOR HYDROGEN SULFIDE MONITORING

(75) Inventors: Andrew Loris Kurkjian, Sugar Land, TX (US); Dexter Mootoo, Houston, TX (US); Wes C. Wofford, Damon, TX (US); Xu Wu, Beijing (CN); Timothy G. J. Jones, Cottenham Cambs (GB); Russell Kane, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 146 days.

(21) Appl. No.: 09/994,199

(22) Filed: Nov. 26, 2001

(65) Prior Publication Data

US 2002/0121370 A1 Sep. 5, 2002

Related U.S. Application Data

(60) Provisional application No. 60/254,509, filed on Dec. 8, 2000.

(51) Int. Cl.
*E21B 47/01* (2006.01)
*E21B 49/10* (2006.01)
*G01N 1/10* (2006.01)
*G01N 33/00* (2006.01)

(52) U.S. Cl. ............ 166/250.05; 166/113; 166/250.11; 166/264; 73/19.01; 73/23.41; 73/152.23; 73/152.55; 436/121

(58) Field of Classification Search ........... 166/250.01, 166/250.05, 250.11, 204, 113; 175/50, 40; 73/152.4, 152.02, 152.08, 152.18, 152.23, 73/152.54, 152.55, 19.01, 19.09, 23.38, 23.41; 436/121

See application file for complete search history.

(56) References Cited

U.S. PATENT DOCUMENTS

| | | | | |
|---|---|---|---|---|
| 2,994,778 A | * | 8/1961 | Marsh | 250/303 |
| 3,780,575 A | | 12/1973 | Urbanosky | |
| 3,859,851 A | | 1/1975 | Urbanosky | |
| 4,154,659 A | | 5/1979 | Zetter | |
| 4,226,693 A | * | 10/1980 | Maes | 204/404 |
| 4,483,397 A | * | 11/1984 | Gray | 166/250.11 |
| 4,501,323 A | * | 2/1985 | Lively et al. | 166/250.11 |
| 4,603,113 A | * | 7/1986 | Bauer | 436/6 |
| 4,605,065 A | * | 8/1986 | Abercrombie | 166/250.11 |
| 4,678,756 A | | 7/1987 | Parks | |
| 4,688,638 A | * | 8/1987 | Williams | 166/250.11 |
| 4,928,760 A | * | 5/1990 | Freitas | 166/113 |
| 4,994,671 A | | 2/1991 | Safinya et al. | |
| 5,095,977 A | * | 3/1992 | Ford | 166/113 |

(Continued)

FOREIGN PATENT DOCUMENTS

GB 1 495 284 A 12/1977

(Continued)

OTHER PUBLICATIONS

Smith Wire Cloth Co., MONEL, 1997.*

(Continued)

*Primary Examiner*—Jennifer H. Gay
(74) *Attorney, Agent, or Firm*—J. L. Jennie Salazar; Victor H. Segura; Brigitte L. Echols

(57) ABSTRACT

The present invention relates to a method and apparatus for detection of hydrogen sulfide in downhole operations. A downhole tool is provided with a coupon adapted to react at varying degrees to exposure to concentrations of hydrogen sulfide. The downhole tool is positioned in the wellbore with the coupon(s) exposed to downhole fluids. A reaction to a change in the coupon, such as coloration, is used to determine the presence and concentration of hydrogen sulfide.

37 Claims, 15 Drawing Sheets

U.S. PATENT DOCUMENTS

| | | | |
|---|---|---|---|
| 5,289,875 | A | 3/1994 | Stokley et al. |
| 5,303,775 | A | 4/1994 | Michaels et al. |
| 5,329,811 | A | 7/1994 | Schultz et al. |
| 5,337,822 | A | 8/1994 | Massie et al. |
| 5,351,532 | A | 10/1994 | Hager |
| 5,397,708 | A | 3/1995 | Lessard et al. |
| 5,529,841 | A | 6/1996 | Neihof |
| 5,627,749 | A | 5/1997 | Waterman et al. |
| 5,635,631 | A | 6/1997 | Yesudas et al. |
| 5,859,430 | A | 1/1999 | Mullins et al. |
| 6,040,406 | A * | 3/2000 | Carrier et al. ......... 526/238.22 |
| 6,223,822 | B1 | 5/2001 | Jones |
| 2003/0134426 | A1* | 7/2003 | Jiang et al. .................. 436/121 |
| 2004/0063215 | A1* | 4/2004 | Horiuchi et al. ............. 436/121 |
| 2004/0159149 | A1* | 8/2004 | Williams et al. ......... 73/152.23 |

FOREIGN PATENT DOCUMENTS

| | | |
|---|---|---|
| GB | 2 344 365 B | 1/2001 |
| GB | 2 359 631 A | 8/2001 |
| WO | WO 99/00575 | 1/1999 |
| WO | WO 99/00575 A2 | 1/1999 |
| WO | WO 01/63094 | 8/2001 |

OTHER PUBLICATIONS

Sulfides, "WildaboutRocks", 2002-2003.*
*Metal Samples/Cortest* by Metal Samples/Cortest Instrument Systems, A Division of Alabama Specialty Products, Inc., undated.
*Metal Samples* by Metal Samples Company, A Division of Alabama Specialty Products, Inc.
Search Report for GB 0129405.7 dated May 24, 2002.
Hart et al., A Disposable Amperometric Gas Sensor for Sulphur-Containing Compounds Based on a Chemically Modified Screen Printed Carbon Electrode Coated with a Hydrogel, Analytica Chimica Acta, 342, 1997, pp. 199-206.
Garrett, R.L., A New Field Method for the Quantitative Determination of Sulfides in Water-Based Drilling Fluids, Journal of Petroleum Technology, Sep. 1977, pp. 1195-1202.
Eckert, W. et al., A New Liquid-Junction Free Probe For the In Situ Determination of pH, $pH_2S$ and Redox Values, Wat. Res. vol. 24, No. 11, 1990, pp. 1341-1346.
Volkan, Murvet et al., A Novel Sorbent Tube for Ambient Hydrogen Sulfide Determination, Talanta 47, 1998, pp. 585-593.
Suleimenov, O.M. et al., A Spectrophotometric Study of Hydrogen Sulphide Ionisation in Aqueous Solutions to 350°, Geochimica et Cosmochimica Acta vol. 61, No. 24, 1997, pp. 5187-5198.
Hadden, David M., A System for Continuous On-Site Measurement of Sulfides in Water-Base Drilling Muds, Society of Petroleum Engineers 6664, Tyler, Texas, Nov. 1977, pp. 81-92.
Jeroschewski, P. et al., An Amperometric Microsensor for the Determination of $H_2S$ in Aquatic Environments, Analytical Chemistry, vol. 68, No. 24, Dec. 15, 1996, pp. 4351-4357.
Ramstad, Tore et al., Analysis of Hydrogen Sulfide Gas from a Pharmaceutical Drug Formulation by Cryofocused Headspace Gas Chromatography, Analyst, Dec. 1995, vol. 120, pp. 2775-2780.
Hachenberg, H. et al., Analytical Applications, Gas Chromatography Headspace Analysis, Wiley, 1984, pp. 1-78.
Arowolo, Toyin A. et al., Automated Determination of Sulphide by Gas-Phase Molecular Absorption Spectrometry, Analyst, Jun. 1991, vol. 116, pp. 595-599.
Devai, I. et al., Changes in Reduced Gaseous Sulfur Compounds Collected in Glass Gas Sampling Bulbs, Analytical Letters, 27(12), 1994, pp. 2403-2411.
Brunner, U. et al., Chromatographic Determination of Phosphine ($PH_3$) and Hydrogen Sulfide ($H_2S$) in the Headspace of Anaerobic Bacterial Enrichments Using Flame Photometric Detection, Chromatographia vol. 40, No. 7/8, Apr. 1995, pp. 399-403.
Bethea, Robert M. et al., Comparison of Hydrogen Sulfide Analysis Techniques, Journal of the Air Pollution Control Association, vol. 23, No. 8, Aug. 1973, pp. 710-713.
Atta, Nada F. et al., Conducting Polymer Ion Sensor Electrodes—III. Potentiometric Sulfide Ion Selective Electrode, Talanta 47 (1998) pp. 987-999.
Tamaki, Jun et al., $CuO-SnO_2$ Elemenet for Highly Sensitive and Selective Detection of $H_2S$, Sensors and Actuators B, 9, 1992, pp. 197-203.
Sberveglieri, G. et al., Detection of sub-ppm $H_2S$ Concentrations by Means of $SnO_2(Pt)$ Thin Films, Grown by the RGTO Technique, Sensors and Actuators B. 15-16, 1993, pp. 86-89.
Knoery et al., Determination of Carbonyl Sulfide and Hydrogen Sulfide Species in Natural Waters Using Specialized Collection Procedures and Gas Chromatography with Flame Photometric Detection, Analytical Chemistry, vol. 65, No. 8, Apr. 15, 1993, pp. 976-982.
Cutter, Gregory A. et al., Determination of Dissolved Sulfide and Sedimentary Sulfur Speciation Using Gas Chromatography-Photoionization Detection, Analytical Chemistry, vol. 59, No. 5, Mar. 1, 1987, pp. 717-721.
Opekar, Frantisek et al., Determination of Gaseous Hydrogen Sulfide by Cathodic Stripping Voltammetry After Preconcentration on a Silver Metalized Porous Membrane Electrode, Analytical Chemistry, vol. 56, No. 8, Jul. 1984, pp. 1206-1209.
Rhodes, Harold L., Determination of Hydrogen Sulfide Content in Natural Gas, Evaluation of Containers for Preparation of Calibration Standards, and Sample Collection Procedure, U.S. Dept. of the Interior, Bureau of Mines, Report of Investigations 8391, Washington, 1979, pp. 1-12.
Masselter et al., Determination of Inorganic Anions in Kraft Pulping Liquors by Capillary Electrophoresis, J. High Resol. Chromatogr., vol. 19, Mar. 1996, pp. 131-136.
Francom, Donna et al., Determination of Low Level Sulfides in Environmental Waters by Automated Gas Dialysis/Methylene Blue Colorimetry, Analytical Letters 22 (11&12), 1989, pp. 2587-2600.
Font, Joaquim, Determination of Sulfide in the Leather Industry by Capillary Electrophoresis, Journal of Chromatography A, 740, 1996, pp. 125-132.
Nagashima, K. et al., Determination of Trace Amounts of Sulfide in Human Serum by High-Performance Liquid Chromatography with Fluorometric Detection After Derivatization with 2-Amino-5-N, N-Diethylaminotoluene and Iron (III), Journal of Liquid Chromatography, 18(3), 1995, pp. 515-526.
Hu, Xiaoya et al., Determination of Trace-Levels of Sulfide by High-Sensitivity Potentiometry with a Carbon Paste Electrode, Analytical Communications, Sep. 1996, vol. 33, pp. 297-298.
Brouwer, Henry et al., Diffusion Method for the Determination of Acid-Volatile Sulfides (AVS) in Sediment, Environmental Toxicology and Chemistry, vol. 13, No. 8, pp. 1273-1275.

Shorthouse, Gary et al., Down Hole Chemical Sensors for Sub-Sea Oil Wells, MST News 2, 1998, pp. 12-13.

Schiavon, Gilberto, Electrochemical Detection of Trace Hydrogen Sulfide in Gaseous Samples by Porous Silver Electrodes Supported on Ion-Exchange Membranes (Solid Polymer Electrolytes), Analytical Chemistry, vol. 67, No. 2, Jan. 15, 1995, pp. 318-323.

Burke, N.E. et al., Extended Analysis of Live Reservoir Oils by Gas Chromatography, Society of Petroleum Engineers 21003, Feb. 20-22, 1991, pp. 79-87.

Choi, Martin M.F. et al., Fluorimetric Optode Membrane for Sulfide Detection, Analyst, Jul. 1998, vol. 123, pp. 1631-1634.

Cardoso, Arnaldo et al., Fluorimetric Fiber Optic Drop Sensor for Atmospheric Hydrogen Sulfide, Talanta 44 (1997), pp. 1099-1106.

Jeroschewski, Paul et al., Galvanic Sensor for Determination of Hydrogen Sulfide, Electroanalysis, 6, 1994, pp. 769-772.

Jeroschewski, Paul et al., Galvanic Sensor for the Determination of Hydrogen Sulphide/Sulphide in Aqueous Media, Fresenius Journal of Analytical Chemistry, 346, 1993, pp. 930-933.

Vitenberg et al., Gas Chromatographic Determination of Trace Amounts of Sulfur Compounds in Industrial Effluents, Analytical Chemistry, vol. 49, No. 1, Jan. 1977, pp. 128-133.

Weldon, V. et al., $H_2S$ and $CO_2$ Gas Sensing Using DFB Laser Diodes Emitting at 1.57 µm, Sensors and Actuators B 29, 1995, pp. 101-107.

Mochida, Tadashi et al., Highly Sensitive and Selective $H_2S$ Gas Sensor From R.F. Sputtered $SnO_2$ Thin Film, Sensors and Actuators B 24-25, 1995, pp. 433-437.

Eroglu, Ahmet E. et al., Hydrogen Sulfide Determination by Solid Surface Luminescence, Fresenius J. Anal. Chem., 1996, 355, pp. 667-671.

Smits, A.R. et al., In-Situ Optical Fluid Analysis as an Aid to Wireline Formation Sampling, SPE Formation Evaluation, 10, 1995, pp. 91-98.

Shanthi, K. et al., Method for Sampling and Analysis of Hydrogen Sulfide, Analyst, May 1996, vol. 121, pp. 647-650.

Kurosawa, H. et al., Microbial Sensor for Selective Determination of Sulphide, Appl. Microbiol. Biotechnol., 41, 1994, pp. 556-559.

Revsbech, Niels Peter et al., Microelectrode Studies of the Photosynthesis and $O_2$, $H_2S$ and pH Profiles of a Microbial Mat, Limnol. Oceanogr., 28(6), 1983, pp. 1062-1074.

Kalpakci, Bayram et al., Mitigation of Reservoir Souring—Decision Process, Society of Petroleum Engineers 28947, San Antonio, Texas, Feb. 14-17, 1995, pp. 29-40.

Badry, Rob et al., New Wireline Formation Tester Techniques and Applications, SPWLA 34th Annual Logging Symposium, Jun. 13-16, 1993, pp. 1-16.

Kuban, Vlastimil et al., Nitroprusside and Methylene Blue Methods for Silicone Membrane Differentiated Flow Injection Determination of Sulfide in Water and Wastewater, Anal. Chem. 1992, 64, pp. 36-43.

Carlson, M. R. et al., Obtaining PVT Data For Very Sour Retrograde Condensate Gas and Volatile Oil Reservoirs: A Multi-Disciplinary Approach, Society of Petroleum Engineers 35653, pp. 691-706.

Spaziani, Michelle A. et al., On-line Determination of Sulfide by the 'Methylene Blue Method' with Diode-Laser-Based Fluorescence Detection, Analyst, Dec. 1997, vol. 122, pp. 1555-1557.

Narayanaswamy, R. et al., Optosensing of Hydrogen Sulphide Through Paper Impregnated with Lead Acetate, Fresnius Z Anal. Chem., 1998, 329, pp. 789-792.

Stern, S.A. et al., Permeability of Silicone Polymers to Ammonia and Hydrogen Sulfide, Journal of Applied Polymer Science, vol. 38, pp. 2131-2147.

Quinn, R. et al., Polyelectrolyte Membranes for Acid Gas Separations, Journal of Membrane Science 131, 1997, pp. 49-60.

Kirchnerova, J. et al., Potentiometric Gaseous Sulfur Sensor Based on Silver Beta-Alumina Solid Electrolyte, Solide State Ionics 91, 1996, pp. 257-264.

Ma, Yi Long et al., Potentiometric Selective Determination of Hydrogen Sulfide by an Electropolymerized Membrane Electrode Based on Binaphthyl-20-crown-6, Analytica Chimica Acta 289, 1994, pp. 21-26.

Dobenik, D. et al., Preparation of a Sulphide Ion-Selective Microelectrode with Chemical Pretreatment of Silver Wire in Hg(II) Solution, Fresenius' Journal of Anal. Chem., 1990, 337, pp. 369-371.

Kolb et al., Principles of Headspace Analysis, Static Headspace-Gas Chromatography, Theory and Practice, Wiley-VCH, 1997, pp. 1-11.

American Petroleum Institute, Recommended Practice Standard Procedure for Field Testing Water-Based Drilling Fluids, API Recommended Practice 13B-1 (RP 13B-1), First Edition, Jun. 1, 1990, pp. 1-46.

Schlumberger Wireline and Testing, Sampling, Houston, Texas, 1996, pp. 10-1 through 10-25.

Parrillo, D.J. et al., Separation of Bulk Hydrogen Sulfide—Hydrogen Mixtures by Selective Surface Flow Membrane, AIChE Journal, Sep. 1997, vol. 43, No. 9, pp. 2239-2245.

Yashin, A. Ya et al., Simultaneous Determination of Sulfide, Iodide, And Rhodanide by Ion Chromatography with the Use of an Amperometric Detector, Journal of Analytical Chemistry, vol. 53, No. 4, 1998, pp. 344-346.

Feng, Guo-Xiang et al., Solubility of $H_2S$ in n-Dodecane, Fluid Phase Equilibria, 87, 1993, pp. 341-346.

Feng, Guo-Xiang et al., Solubility of $H_2S$ in n-Hexadecane at Elevated Pressure, Canadian Journal of Chemical Engineering, vol. 71, Apr. 1993, pp. 327-328.

Yokoyama, Chiaki et al., Solubility of Hydrogen Sulfide in Isooctane, n-decane, n-tridecane, n-hexadecane and squalane at Temperatures From 323 to 523 K and Pressures Up to 1.6 Mpa, Fluid Phase Equilibria, 85, 1993, pp. 257-269.

Feng, Guo-Xiang et al., Solubility of Hydrogen Sulfide in n-Eicosane at Elevated Pressure, J. Chem. Eng. data, 1992, 37, pp. 412-413.

Suleimenov, O.M. et al., Solubility of Hydrogen Sulfide in Pure Water and in NaCL Solutions, From 20 to 320°C and at Saturation Pressures, Geochmica et Cosmochimica Acta, vol. 58, No. 11, pp. 2433-2444.

Tremper, Kevin K. et al., Solubility of Inorganic Gases in High-Boiling Hydrocarbon Solvents, Journal of Chemical and Engineering Data, vol. 21, No. 3, 1976, pp. 295-299.

Aplin, Andrew C. et al., Sour Gas and Water Chemistry of the Bridport Sands Reservoir, Wytch Farm, UK, The Geochemistry of Reservoirs, pp. 303-314.

Haland et al., An Empirical Correleation Between Reservoir Temperature and the Concentration of Hydrogen Sulfide, Society of Petroleum Engineers 50763, Houston, Texas, Feb. 1999, pp. 589-596.

Tissot et al., Geochemical Regularities in Relation to Thermal Evolutionh, Petroleum Formation and Occurrence, 2nd Edition, Springer-Verlag, Berlin, 1984, pp. 453-455.

Kolb, Bruno et al., Special Measurements, Static Headspace—Gas Chromatography Theory and Practice, Wiley-VCH, 1997, pp. 268-270.

Dake, L.P., The Appraisal of Oil and Gas Fields, The Practice of Reservoir Engineering, Elsevier, 1994, pp. 29-44.

Ives, David et al., The Glass Electrode, Reference Electrodes, Theory and Practice, Academic Press, 1961, pp. 238-240.

Myers, Rollie J., The New Low Value for the Second Dissociation Constant for $H_2S$, Journal of Chemical Education, vol. 63, No. 8, Aug. 1986, pp. 687-690.

King, M.B. et al., The Solubilities of Carbon Dioxide, Hydrogen Sulphide and Propane in Some Normal Alkane Solvents—I, Chemical Engineering Science, 1977, vol. 32, pp. 1241-1246.

Feng, G. et al., The Solubility of Hydrogen Sulfide in Mixtures of n-Hexadecane and n-Eicosane, Canadian Journal of Chemical Engineering, 73, 1995, pp. 145-155.

Carroll, John J. et al., The Solubility of Hydrogen Sulphide in Water from 0 to 90°C and Pressures to 1 Mpa, Geochimica et Cosmochimica Acta, 53, 1989, pp. 1163-1170.

Ioffe et al., Theory of Gas-Chromatographic Head-Space Analysis, Head-Space Analysis and Related Methods in Gas Chromatography, Wiley-Interscience, 1984, pp. 9-66.

Goar, B. Gene et al., Large-Plant Sulfur Recovery Processess Stress Efficiency, Oil and Gas Journal, May 23, 1994, pp. 61-67.

Scott, P.J.B. et al., Souring of New Irian Jaya Wells Traced to Indigenous Bacteria, Oil & Gas Journal, Jun. 14, 1993, pp. 47-50.

Vivit, Davison V. et al., Specific-Ion Electrode Determinations of Sulfide Preconcentrated from San Francisco Bay Waters, Environ. Geol. Water Sci. vol. 6, No. 2, pp. 79-90.

Cline, Joel D., Spectrophotometric Determination of Hydrogen Sulfide in Natural Waters, Limnol. Oceanogr., 14, 1969, pp. 454-458.

Koh, Tomozo et al., Spectrophotometric Determination of Sulfide at the $10^{-6}$ mol $I^{-1}$ Level by Formation of Thiocyanate and Its Solvent Extraction with Methylene Blue, Analytical Sciences, Aug. 1993, vol. 9, pp. 487-492.

Mousavi, M.F. et al., Spectrophotometric Determination of Trace Amounts of Sulfide Ion Based on its Catalytic Reduction Reaction with Methylene Blue in the Presence of TE(IV), Analytical Letters, 30(8), pp. 1567-1578.

Cutter, Gregory A. et al., Sulfide in Surface Waters of the Western Atlantic Ocean, Geophysical Research Letters, vol. 15, No. 12, Nov. 1988, pp. 1393-1396.

Howard, A.g. et al., Sulfide Measurement by Flow Injection Analysis with Flame Photometric Detection, Anal. Chem. 1998, 70, pp. 4868-4872.

Rey, Jorge R. et al., Sulfide Variation in the Pore and Surface Waters of Artificial Salt-Marsh Ditches and a Natural Tidal Creek, Estuaries vol. 15, No. 3, Sep. 1992, pp. 257-269.

Dosher, John R. et al., Sulfur Increase Seen Mostly in Heavy Fractions of Lower-Quality Crudes, Oil & Gas Journal, May 23, 1994, pp. 43-48.

Habicht, Kirsten S. et al., Sulfur Isotope Fractionation During Bacterial Sulfate Reduction in Organic-Rich Sediments, Geochimica et Cosmochimica Acta, vol. 61, No. 24, 1997, pp. 5351-5361.

Saltzman, Robert S. et al., Sulfur Recovery Tail Gas Analyses with a Process Diode Array Analyzer, Paper #91-0408, 1991, pp. 733-750.

Hassan, Sayed, Sulfur Specification: Methodology and Application to Sulfide Oxidation Studies at the Sediment-Water Interface, Chemosphere, vol. 29, No. 12, pp. 2555-2569.

Barrett, E.P.S. et al., The Mechanism of Operation of $WO_3$-Based $H_2S$ Sensors, Sensors and Actuators, B1, 1990, pp. 116-120.

Galipeau, J.D. et al., Theory, Design and Operation of a Surface Acoustic Wave Hydrogen Sulfide Microsensor, Sensors and Actuators B 24-25, 1995, pp. 49-53.

Phillips, B.M., Measurement and Distribution of Insterstitial and Overlying Water Ammonia and Hydrogen Sulfide in Sediment Toxicity Tests, Marine Environmental Research, vol. 44, No. 2, 1997, pp. 117-126.

Orr, Wilson L. et al., Geochemistry of Sulfur in Petroleum Systems, ACS Symposium Series 429, American Chemical Society, Washington, D.C. 1990, pp. 2-29.

* cited by examiner

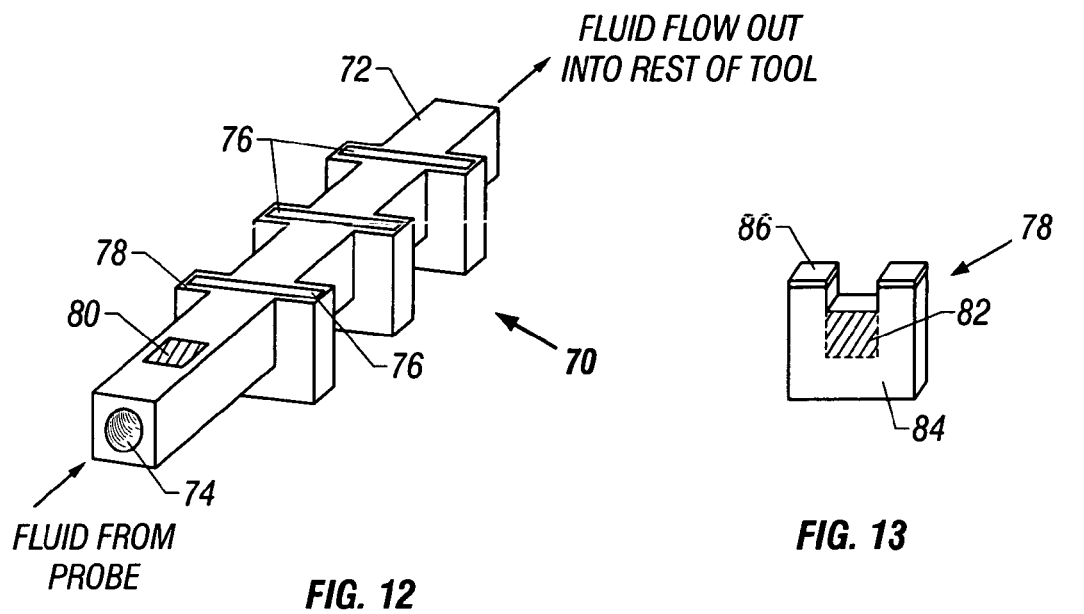
FIG. 12
FIG. 13
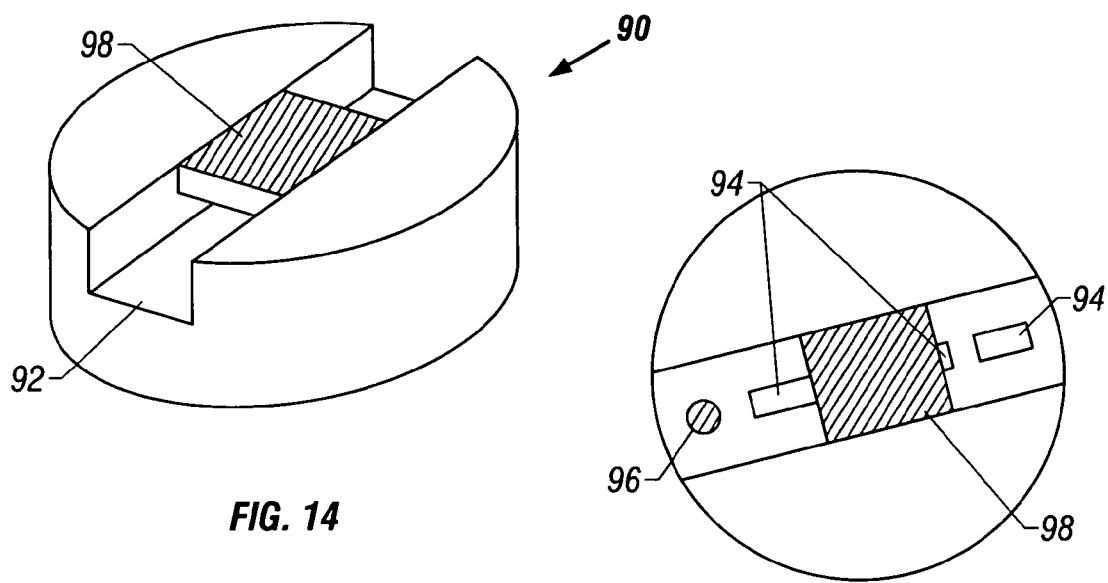
FIG. 14
FIG. 15

| ALLOY | Ni | Cu | Fe | Cr | Mo |
|---|---|---|---|---|---|
| MONEL ALLOY 400 N04400 | 63-70 | BAL. | 2.5 MAX. | -- | -- |
| CUPRONICKEL 70-30 C71500 | 29-33 | BAL. | 0.4 - 1.0 | -- | -- |
| CUPRONICKEL 90-10 C70600 | 9-11 | 86.5 MIN. | 1.0 - 1.8 | -- | -- |
| NICKEL ALLOY 200 N02200 | 99.0 MIN. | 0.25 MAX. | 0.40 MAX. | -- | -- |
| ALLOY B N10001 | BAL. | -- | 6.0 MAX. | 1.0 MAX. | 26 - 33 |
| INCOLOY ALLOY 600 N06600 | 72 MIN. | .50 MAX. | 6 - 10 | 14 - 17 | -- |
| 5CR STEEL K41545 | -- | -- | BAL. | 4 - 6 | 0.45 - 0.65 |
| 9CR STEEL K90941 | -- | -- | BAL. | 8 - 10 | 0.9 - 1.1 |
| 12CR STEEL S41000 | -- | -- | BAL. | 11.5 - 13.5 | -- |

FIG. 16

| TEST NO. | H2S (PPM) | DURATION (HR.) | TEMP. (F) | MONEL 400 | 70/30 CuNi | 90/10 Cu/Ni | NI 200 | ALLOY 600 | ALLOY B |
|---|---|---|---|---|---|---|---|---|---|
| | | | | | CONDITION OF COUPONS AFTER EXPOSURE | | | | |
| 1* | 0 | 6 | 250 | 0 | 0 | ST | — | — | — |
| 2* | 0 | 2 | 400 | 0 | ST | ST | — | — | — |
| 3 | 0 | 2 | 250 | ST | ST | ST | — | — | — |
| 4 | 50 | 2 | 250 | G | DG | DG | — | — | — |
| 5 | 0 | 2 | 300 | ST | ST | ST | — | — | — |
| 6 | 50 | 2 | 300 | DG | G | DG | — | — | — |
| 7 | 0 | 2 | 350 | ST | ST | ST | — | — | — |
| 8 | 50 | 2 | 350 | DG | G | DG | — | — | — |
| 9 | 0 | 2 | 400 | DG | G | G | — | — | — |
| 10 | 50 | 6 | 400 | DG | G | DG | — | — | — |
| 11 | 25 | 2 | 300 | DG | G | G | — | — | — |
| 12 | 25 | 2 | 300 | DG | G | G | — | — | — |
| 13 | 10 | 2 | 300 | DG | G | DG | — | — | — |
| 14 | 10 | 2 | 300 | DG | G | DG | — | — | — |
| 15 | 5 | 2 | 300 | DG | G | DG | — | — | — |
| 16 | 25 | 2 | 300 | DG | G | G | G | ST | DG |
| 17 | 10 | 2 | 300 | DG | G | DG | ST | ST | ST |
| 18 | 18 | 2 | 300 | DG | G | G | ST | ST | G |

NOTES :
O - NO ATTACK
ST - SLIGHT TARNISH
G - GRAY CORROSION FILM
DG - DARK GRAY CORROSION FILM

* TEST CONTAINED OIL MUD AS LIQUID PHASE

*FIG. 17*

| TEST NO. | H₂S (PPM) | DURATION (HR.) | TEMP. (F) | 5Cr | 9Cr | 12Cr | 316 SS | Ni200 | ALLOY 600 | ALLOY B |
|---|---|---|---|---|---|---|---|---|---|---|
| | | | | \multicolumn{7}{c}{CONDITION OF COUPONS AFTER EXPOSURE} |
| 201* | 25 | 2 | 250 | G | G | G | O | DG | T | B |
| 301* | 50 | 2 | 250 | G | G | G | O | G | T | G |
| 401 | 25 | 2 | 250 | G | G | G | G | G | G | DG |
| 501 | 50 | 2 | 250 | DG | DG | DG/B | LG | G | G | DG |
| 601 | 100 | 2 | 250 | DG/B | DG/B | B | LG | G | B | G |
| 701 | 50 | 2 | 250 | DG | DG | DG | LG | G | G | G |
| 801 | 75 | 2 | 250 | DG | DG | DG | LG | LG | DG | LG |
| 901 | 100 | 2 | 300 | DG | G | DG | LG | G | B | G |
| 1001 | 75 | 2 | 300 | DG | DG | DG | LG | LG | B | G |
| 1101 | 50 | 2 | 300 | DG | DG | DG | LG | LG | B | G |
| 1201 | 100 | 2 | 250 | G/B | G/B | G/B | LG | LG | BB | G |
| 1301 | 75 | 2 | 300 | DG | DG | G | G | G | B | G |
| 1401 | 50 | 2 | 350 | DG | DG | DG | G | G | DG | G |
| 1501 | 75 | 2 | 350 | DG | DG | DG | G | LG | G | DG |
| 1601 | 100 | 2 | 350 | G/B | DG | DG | G | G | G | G |

NOTEES.:
O - NO ATTACK
ST - SLIGHT TARNISH
LG - LIGHT GRAY CORROSION FILM
G - GRAY CORROSION FILM
DG - DARK GRAY CORROSION FILM
B - BLACK CORROSION FILM

* COUPONS IN VAPOR PHASE

FIG. 18

METHOD AND APPARATUS FOR HYDROGEN SULFIDE MONITORING

This application claims priority from Provisional Application No. 60/254,509, filed Dec. 8, 2000, the contents of which is hereby incorporated by reference in its entirety.

BACKGROUND OF THE INVENTION

1. Field of the Invention

This invention relates generally to the identification of corrosive materials in a wellbore penetrating a subsurface formation and, more particularly, to the identification of hydrogen sulfide ($H_2S$) in such a wellbore and contained within formation fluids.

2. Description of Related Art

Hydrocarbon fluids such as oil and natural gas are obtained from a subterranean geologic formation, referred to as a reservoir, by drilling a well that penetrates the hydrocarbon-bearing formation. Once a wellbore has been drilled, the well must be completed before hydrocarbons can be produced from the well. A well completion involves the design, selection, and installation of equipment and materials in or around the wellbore for conveying, pumping, and/or controlling the production or injection of fluids. After the well has been completed, production of oil and gas can begin.

In the construction of hydrocarbon production, processing and transportation facilities, it is often desirable to know whether corrosive materials are contained within the formation fluids in order to select the appropriate materials for the design of wellbore completions, pipelines and related facilities. In particular, it may be necessary to know the concentration of any hydrogen sulfide contained within the formation fluids if the proper materials are to be used.

The desirability of taking downhole formation fluid samples for chemical and physical analysis has long been recognized by oil companies, and such sampling has been performed by the assignee of the present invention, Schlumberger, for many years. Samples of formation fluid, also known as reservoir fluid, are typically collected as early as possible in the life of a reservoir for analysis at the surface and, more particularly, in specialized laboratories. The information that such analysis provides is vital in the planning and development of hydrocarbon reservoirs, as well as in the assessment of a reservoir's capacity and performance.

The process of wellbore sampling involves the lowering of a sampling tool, such as the MDT™ formation testing tool, owned and provided by Schlumberger, into the wellbore to collect a sample or multiple samples of formation fluid by engagement between a probe member of the sampling tool and the wall of the wellbore. The sampling tool creates a pressure differential across such engagement to induce formation fluid flow into one or more sample chambers within the sampling tool. This and similar processes are described in U.S. Pat. Nos. 4,860,581; 4,936,139 (both assigned to Schlumberger); U.S. Pat. Nos. 5,303,775; 5,377,755 (both assigned to Western Atlas); and U.S. Pat. No. 5,934,374 (assigned to Halliburton).

The metals comprising the MDT tool and other known formation testing tools are known to react with any hydrogen sulfide ($H_2S$) in the fluid coming from the formation. Because of this reaction, when a fluid sample from the MDT tool (which will be described for illustrative purposes hereinafter) is subsequently analyzed, the measured concentration of $H_2S$ in the sample is lower than the concentration of $H_2S$ in the reservoir fluid. If the concentration of $H_2S$ in the reservoir fluid is sufficiently low, the concentration in the fluid sample can have no measurable $H_2S$.

Customers (i.e., oil companies) often want to know the concentration of $H_2S$ in order to select the appropriate materials for the design of completions, pipelines and facilities. $H_2S$—resistant materials can be 5–50 times more expensive than non-resistant materials, so money is wasted if they are used but not needed. The consequences may be worse if they are not used but were needed. Normally, in the latter cases, production is stopped, an expensive well intervention is required, and then the expensive materials must be used.

It difficult, if not impossible and/or impracticable, to correct the concentration of $H_2S$ in the sample for that which was lost due to reaction with the metal in the MDT tool. The mechanisms are too complex and depend on concentration, materials, pressure, temperature, history, etc. Furthermore, if there is no $H_2S$ in the sample, it is usually not possible to tell if there was $H_2S$ in the reservoir fluid or not.

An alternative would be to make the MDT tool non-reactive, or inert, to $H_2S$. A bottom-hole sampler can be thought of as a sample bottle that sits in the production stream. The seal valve opens, the bottle fills and the bottle re-seals. If the inner walls of the bottle are coated or passivated in some manner, then the $H_2S$ concentration of the fluid that enters the bottle will remain in the fluid. In this way, a lab analysis can determine the concentration of $H_2S$ in the reservoir fluid.

The MDT tool differs in that fluid is pumped along the flowline, through the displacement unit, and then out to the wellbore for an extended period of time, prior to the sample being captured in a bottle. If at the time when the sample is to be captured, the concentration of $H_2S$ at the location of the sample chamber is equal, or close to, the concentration of $H_2S$ entering the distant probe, then it may be sensible to coat or passivate an MDT tool bottle to preserve the concentration. If, however, the concentration of $H_2S$ at the location of the sample chamber is lower than the level in the formation, then there is no point attempting to preserve the $H_2S$ in the sample. (It may not be realistic to consider coating or passivating the entire flow path from the probe to the sample bottle.) In this case, a downhole $H_2S$ sensor positioned close to the sandface, may be required.

Tests have been performed to determine if a coated sample bottle will meet the customer need, or whether a downhole sensor will be required. To make this decision, tests of the $H_2S$ loss within the flowline and displacement unit my be experimentally measured. The results show that the loss of $H_2S$ within the flowline and in the displacement unit is significant. Hence, a downhole sensor located near the probe is deemed desirable.

Sulfide Stress Cracking

Sulfide stress cracking (stress corrosion cracking, hydrogen embrittlement) refers to the combination of hydrogen sulfide and water reacting with metal to form micro-cracks. These cracks weaken the material. If the material is also under tensile stress, the strength of the material may reduce to the point of failure. This form of corrosion is unlike 'weight loss' $CO_2$ induced mechanisms of corrosion, in which the metal dissolves, lowering its strength until failure occurs.

If the material is not under tensile load, or if there is no water present, then the presence of hydrogen sulfide will usually not cause material failure.

NACE MR0175 states that an $H_2S$ partial pressure of 0.05 psi or more requires the use of $H_2S$—resistant materials. A graphical depiction of the NACE specification is shown in FIG. 1.

The relationship between partial pressure and concentration is set forth below:

Partial Pressure=Concentration×Absolute Pressure

For example, a concentration of 10 ppm is 10/1,000,000 or $1 \times 10^{-5}$. For an absolute pressure of 10,000 psi, the partial pressure is $10,000 \times 10^{-5} = 0.1$ psi. Therefore, 10 ppm at 10 kpsi is twice the NACE MR0175 limit of 0.05 psi. This example corresponds to the point A on the plot SHOWN in FIG. 1.

As mentioned above, sulfide stress cracking of will not occur without water (and tensile stress) also being present. Since the development of MR0175, it has been discovered that the severity of the problem depends on the pH of the water, in addition to the partial pressure of $H_2S$. This is illustrated in FIG. 2. Region 0 (below 0.05 psi partial pressure) is referred to as 'sweet', and no special resistant materials are required. Regions 1, 2 and 3 of FIG. 2 are referred to as 'mild sour', 'intermediate sour' and 'severe sour', and materials with increasing levels of resistant materials are required.

$H_2S$-Resistant Materials

The word '$H_2S$ resistant' means that the material does not form micro-cracks that weaken the material. However, the material may still 'react' with $H_2S$. Thus, a non-reactive or inert, material is also $H_2S$—resistant, but the reverse may not be true.

Leading Causes of Mechanical Failure

The leading causes of mechanical failure of materials in the oil and gas industry are estimated as follows:

| | |
|---|---|
| 28% | CO2 corrosion |
| 18% | $H_2S$ sulfide stress cracking |
| 18% | welding |
| 15% | pitting |
| 12% | erosion |
| 6% | galvanic |
| 3% | stress. |

Sulfide stress cracking is estimated to be the second leading cause of mechanical failure.

The consequences of a mechanical failure to the customer are generally severe. A failure within a production facility at surface may require that the production be stopped. A failure in a well completion or a sub-sea pipeline requires a much more difficult and expensive intervention, in addition to shutting in the production.

Cost of $H_2S$—Resistant Materials

Referring now to FIG. 3, the table shows the cost in dollars per pound of various alloys. The more expensive alloys are $H_2S$ resistant and range from 10 to 60 times more than the least expensive, which are not $H_2S$ resistant. Hence, customers often wish to know whether or not the expensive alloys are needed. The consequence of using of these expensive materials in a case where they are not needed is a significant wasted capital expenditure. The consequence of not using them in a case where they are needed may be much worse.

Experiment Design and Results

The merits of an experimental approach have been documented. For example, tests have been done at 1000 psi and 300 deg F. Nitrogen gas, water vapor and 50 ppm $H_2S$ were used as the test fluid. This corresponds to a partial pressure of 0.05 psi, which is the threshold between 'sweet' and 'sour'.

There were 4 series of tests conducted:
1. Flowline MONEL® test
2. Flowline titanium test
3. Elastomer test
4. Displacement unit test The flowline tests were conducted by flowing the fluid through 20 feet of tubing at a flowrate of 1 liter/minute. The concentration of $H_2S$ at the output was measured periodically by sampling the output. The sampling was frequent at early times, and less frequent at late times.

The test duration was 4 hours. Two different tubings were tested, and a repeat test was done on one of the two tubings.

FIGS. 4 and 5 are representative of the behavior of the MONEL® and Titanium sections of the flowline, respectively. Here we see that, after pumping 50 ppm $H_2S$ through the MONEL® tube for 4 hours, only 12 ppm is coming out, while the Titanium is nearly non-reactive.

Elastomer buttons and slabs were tested for their tendency to 'soak up' $H_2S$ with time. The buttons had 80% less area and 50% less volume than the slabs. The results depicted in FIGS. 6 and 7 show little absorption over 10 minutes, but considerable absorption over 1000 minutes (16 hours). The difference in absorption between the slabs and the buttons was 30%, which is closer to the difference in volume than the difference in area. Therefore, the absorption is more of a volume effect (i.e. a sponge-like behavior).

The displacement unit differs from the flowline in that the fluid is resident on the same material for roughly 30 seconds. The displacement unit is made from both MONEL® and Aluminum-Bronze, and it clear from FIG. 8 that the displacement unit extracts 16 ppm of the $H_2S$ within 30 seconds and all 50 ppm of the $H_2S$ from the fluid within an hour.

Customers may need to know the concentration of hydrogen sulfide in the reservoir fluid. Fluid samples from the MDT tool contain a concentration of $H_2S$ that is less than that of the reservoir fluid. One solution would be to develop an 'inert' or 'non-reactive' sample bottle that can preserve the concentration of $H_2S$ in the fluid. However this only makes sense if the reaction along the flowline, and within the displacement unit, have not already reduced the concentration of $H_2S$. If the concentration of $H_2S$ at the location of the sample bottle is not equal (or close to) the concentration entering the probe, then an $H_2S$ sensor positioned near the sandface may be required.

A series of flowline, elastomer and displacement unit tests were concluded. The results indicate that both the displacement unit and the MONEL® sections of the flowline react significantly with any $H_2S$ in the fluid. Therefore, even after a significant pump-out period, the concentration of $H_2S$ at the location of the sample bottle may not be representative of the level which is entering the probe. An $H_2S$ sensor positioned near the sandface may be required. Thus, the development of a non-reactive bottle may be desirable.

If $H_2S$ is present in an MDT tool fluid sample in a PVT lab analysis (or at the well site), there may be a higher concentration of $H_2S$ in the reservoir fluid, and may be an issue for both personal safety and materials selection. If $H_2S$ is not present in an MDT tool fluid sample, then it will often be unclear if there is enough $H_2S$ present in the reservoir fluid to pose a risk to personal safety, or to require special materials selection.

Various techniques have been developed to detect Hydrogen Sulfide in wellbore applications. Such techniques include at least the following: gas chromatography, potentiometrics, cathode stripping, spectrophotometry, spectroscopy, reflectivity, fluorescent reagents, biosensors, chemical sensors, etc. as described in PCT International Application No. PCT/GB/0011 to Jiang et al. published on Aug. 30, 2001, the entire contents of which is hereby incorporated by reference. Some techniques, such as PCT International Application No. PCT/GB/0011 and U.S. Pat. No. 6,223,922 B1 issued on May 1, 2001 to Jones, the entire contents of which are hereby incorporated by reference, relate to downhole operations. The current means of taking fluid samples for hydrogen sulfide analysis can alter the hydrogen sulfide content in the sample and can provide the operator with erroneous results that cannot be relied on.

There remains a need for downhole sensors that can measure $H_2S$ concentration in fluid under temperature and pressure. The present invention addresses these shortcomings.

SUMMARY OF THE INVENTION

One embodiment of the present invention is a method of identifying the presence of hydrogen sulfide in fluid produced from a reservoir. The method comprises providing a tool comprising at least one sample of material that is optically reactive to the presence of hydrogen sulfide and exposing the at least one sample of material to a sample of reservoir fluid upon the fluid production from the reservoir.

An alternate embodiment of the present invention is a method for identifying the presence of hydrogen sulfide in a subsurface formation penetrated by a wellbore. The method comprises lowering a downhole tool into the wellbore, the tool comprising a housing, at least one sample of material that is optically reactive to the presence of hydrogen sulfide and at least one passage for conducting formation fluid to the sample of material. Formation fluid is delivered to the sample of material via the passage. The downhole tool is retrieved from the wellbore and the sample of material is inspected to determine if the wellbore fluid contained hydrogen sulfide.

An alternate embodiment is a method for identifying the presence of hydrogen sulfide in a subsurface formation penetrated by a wellbore, comprising the steps of: lowering a downhole tool into the wellbore, the tool including a housing having at least one sample of material that is reactive to the presence of hydrogen sulfide and a passage for conducting formation fluid to the sample of material; delivering formation fluid to the sample of material via the passage; retrieving the downhole tool from the wellbore; and inspecting the sample of material to determine if the wellbore fluid contained hydrogen sulfide.

Yet another embodiment of the invention is a method of reservoir analysis comprising providing a downhole tool comprising at least one sample of material that is optically reactive to the presence of hydrogen sulfide. The downhole tool is lowered into a wellbore that penetrates a reservoir and formation fluid is flowed through the downhole tool. The at least one sample of material is exposed to formation fluid upon the formation fluid entry into the wellbore. Temperature readings of the formation fluid are taken and formation fluid samples are collected within the downhole tool. The downhole tool is retrieved from the wellbore and the optical change of the at least one sample of material is inspected for exposure to hydrogen sulfide contained in the formation fluid. The hydrogen sulfide content of the formation fluid within the reservoir is estimated utilizing the inspection of the optical change of the at least one sample of material and the temperature readings of the formation fluid.

An alternate embodiment of the present invention is an apparatus comprising a housing and at least one sample of material that is optically reactive to the presence of hydrogen sulfide is positioned in the housing, wherein the at least one sample of material is adapted to be exposed to reservoir fluid upon the reservoir fluid entry into the apparatus.

Still another embodiment is a downhole tool comprising a plurality of coupons that are optically reactive to the presence of hydrogen sulfide, a housing capable of retaining the coupons and having a passage for communicating formation fluids between a wellbore and the coupons, a temperature sensor, and a pump capable of flowing formation fluids through the passage and through the downhole tool. When the formation fluids are pumped through the downhole tool the coupons are exposed to the formation fluid upon the formation fluid entry into the downhole tool and the surface of the plurality of coupons are capable of changing color upon contact with hydrogen sulfide and can be interpreted to determine the hydrogen sulfide content in the formation fluids.

Yet another embodiment of the invention is an apparatus for identifying the presence of hydrogen sulfide in a wellbore penetrating a subsurface formation, comprising: a downhole tool including a housing having at least one sample of material that is reactive to the presence of hydrogen sulfide and a passage for conducting formation fluid to the sample of material when the downhole tool is lowered into the wellbore and a hydraulic assembly for delivering formation fluid to the sample of material via the passage.

BRIEF DESCRIPTION OF THE DRAWINGS

The manner in which the present invention attains the above recited features, advantages, and objects can be understood in detail by reference to the preferred embodiments thereof which are illustrated in the accompanying drawings.

It should be noted, however, that the appended drawings illustrate only typical embodiments of this invention and are therefore not to be considered limiting of its scope, for the invention may admit to other equally effective embodiments.

In the drawings:

FIG. 1 is a graphic illustrations of the relationship between partial pressure and concentration for hydrogen sulfide;

FIG. 2 is a graphic illustration of the relationship between pH and partial pressure depicting the related sour regions for hydrogen sulfide;

FIG. 3 is table of various alloys and related price per pound;

FIG. 4 is a graphic illustration of the relationship between hydrogen sulfide concentration and time for a MONEL® Tube with 50 ppm test gas;

FIG. 5 is a graphic illustration of the relationship between hydrogen sulfide concentration and time for a Titanium Tube with 50 ppm test gas;

FIG. 6 is a graphic illustration of the relationship between hydrogen sulfide concentration and time for Elastomer Slabs with 50 ppm test gas;

FIG. 7 is a graphic illustration of the relationship between hydrogen sulfide concentration and time for Elastomer Buttons with 50 ppm test gas;

FIG. 8 is a graphic illustration of the relationship between hydrogen sulfide concentration and time for Displacement Unit (Side 1) with 50 ppm test gas;

FIG. 9 is a schematic illustration of a downhole tool comprising a testing cell in accordance with the present invention;

FIG. 10 is perspective view of an embodiment of the testing cell of FIG. 9;

FIG. 11 is a detailed view of the testing cell of FIG. 10;

Figure 23:
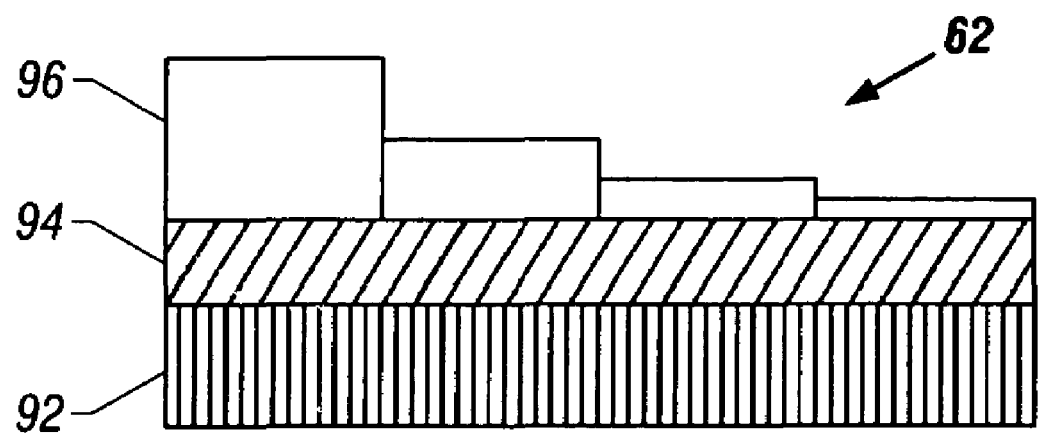

FIG. 12 is a schematic illustration of an alternate embodiment of a testing cell in accordance with the present invention;

FIG. 13 is a perspective view of a coupon used with the testing cell of FIG. 12;

FIG. 14 shows a perspective view of an alternate embodiment of a testing cell having a reaction sensor;

FIG. 15 shows a plan view of the testing cell of FIG. 14;

FIG. 16 is a chart illustrating the list of materials tested in a study of hydrogen sulfide detection;

FIG. 17 is a chart illustrating results of the test of a group of materials from FIG. 20;

FIG. 18 is a chart illustrating results of the test of a group of materials from FIG. 20;

FIGS. 19 through 22 are pictorial views of coupons illustrating the optical reaction of certain metals at various ppm of hydrogen sulfide; and FIG. 23 is a plan view of hydrogen sulfide detection tape.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
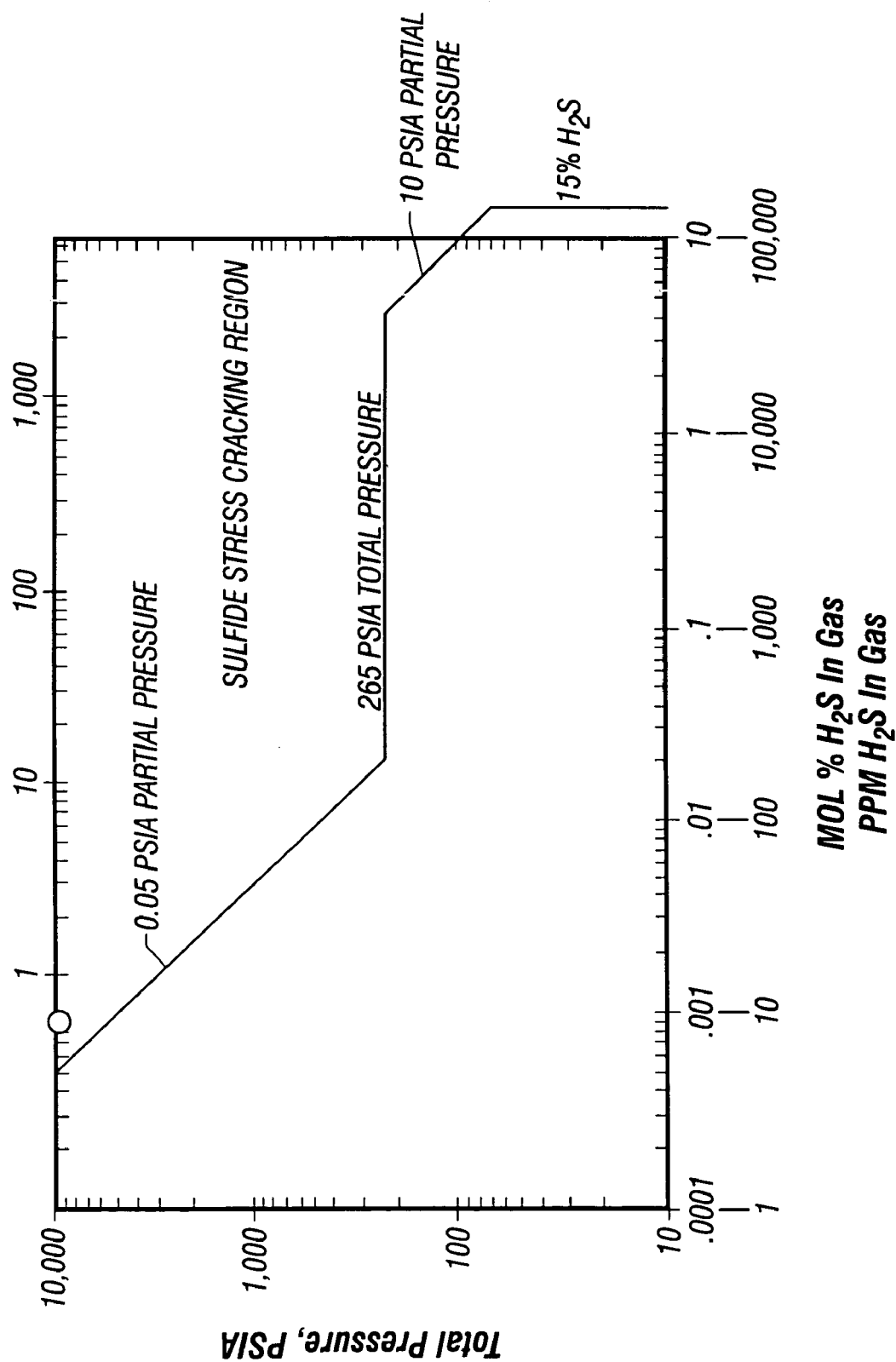
Figures 2, 3:
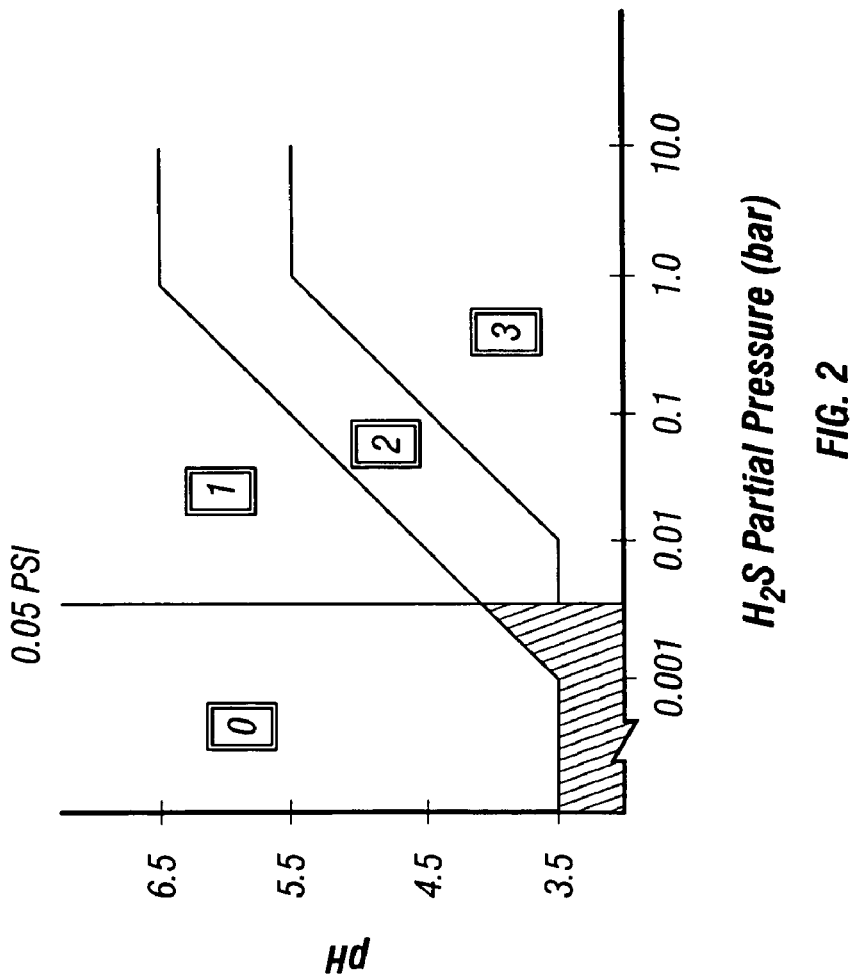
Figure 4:
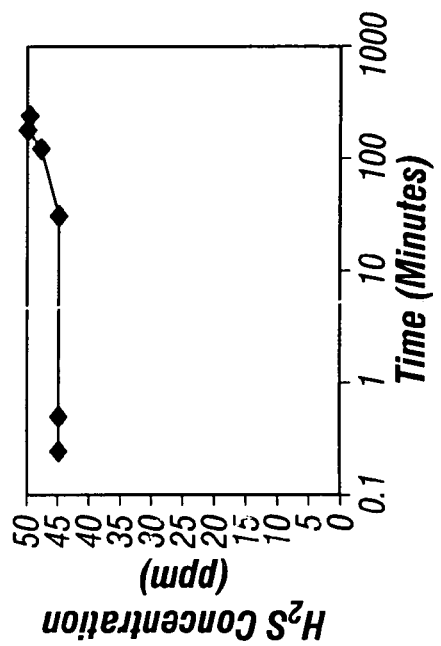
Figure 5:
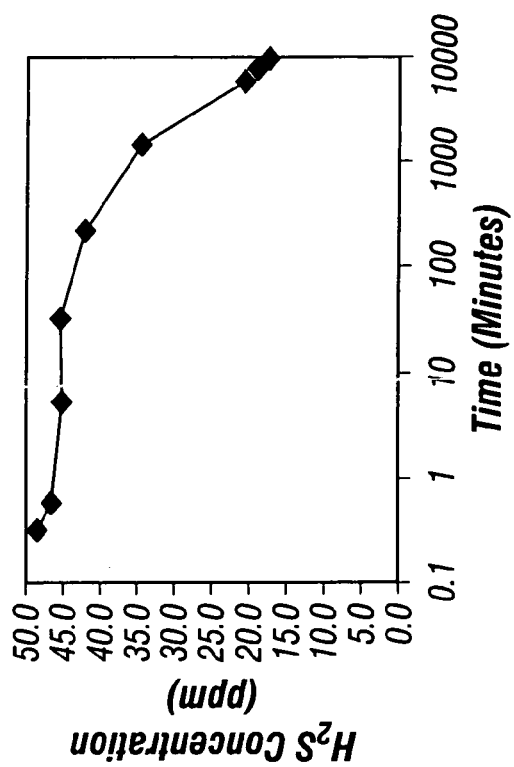
Figure 6:
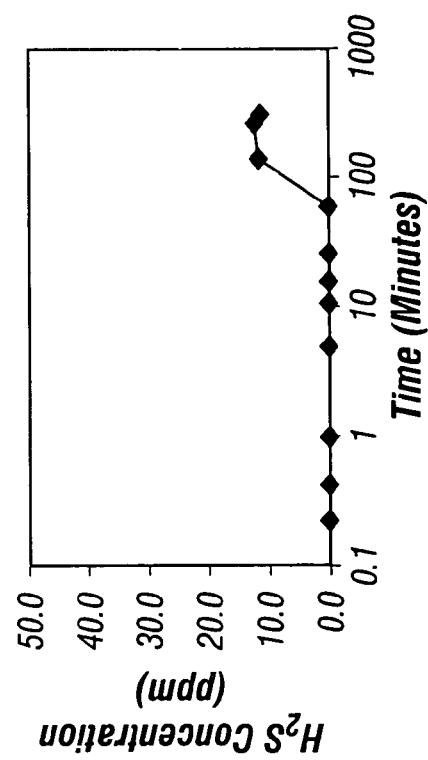
Figure 7:
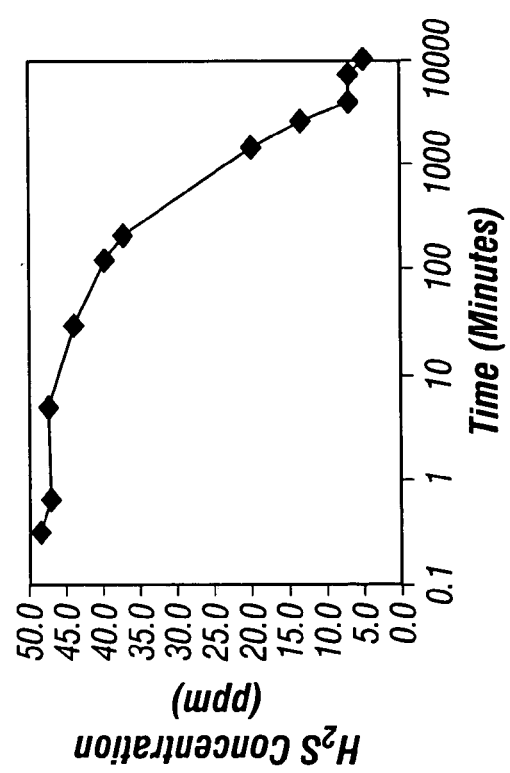
Figure 8:
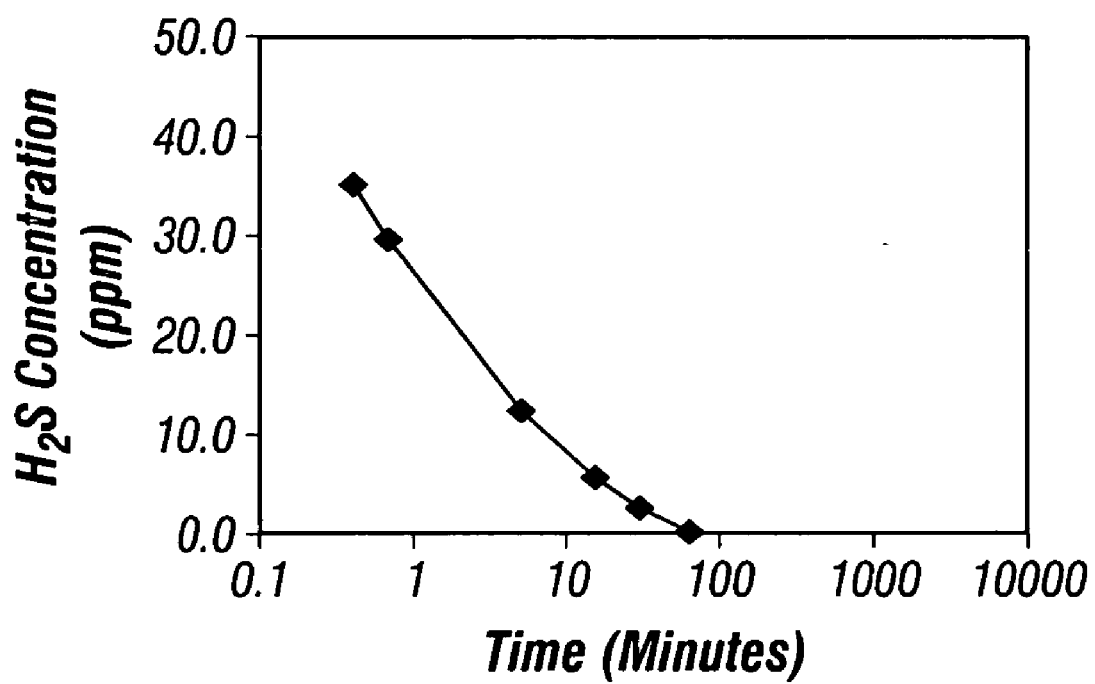
Figure 9:
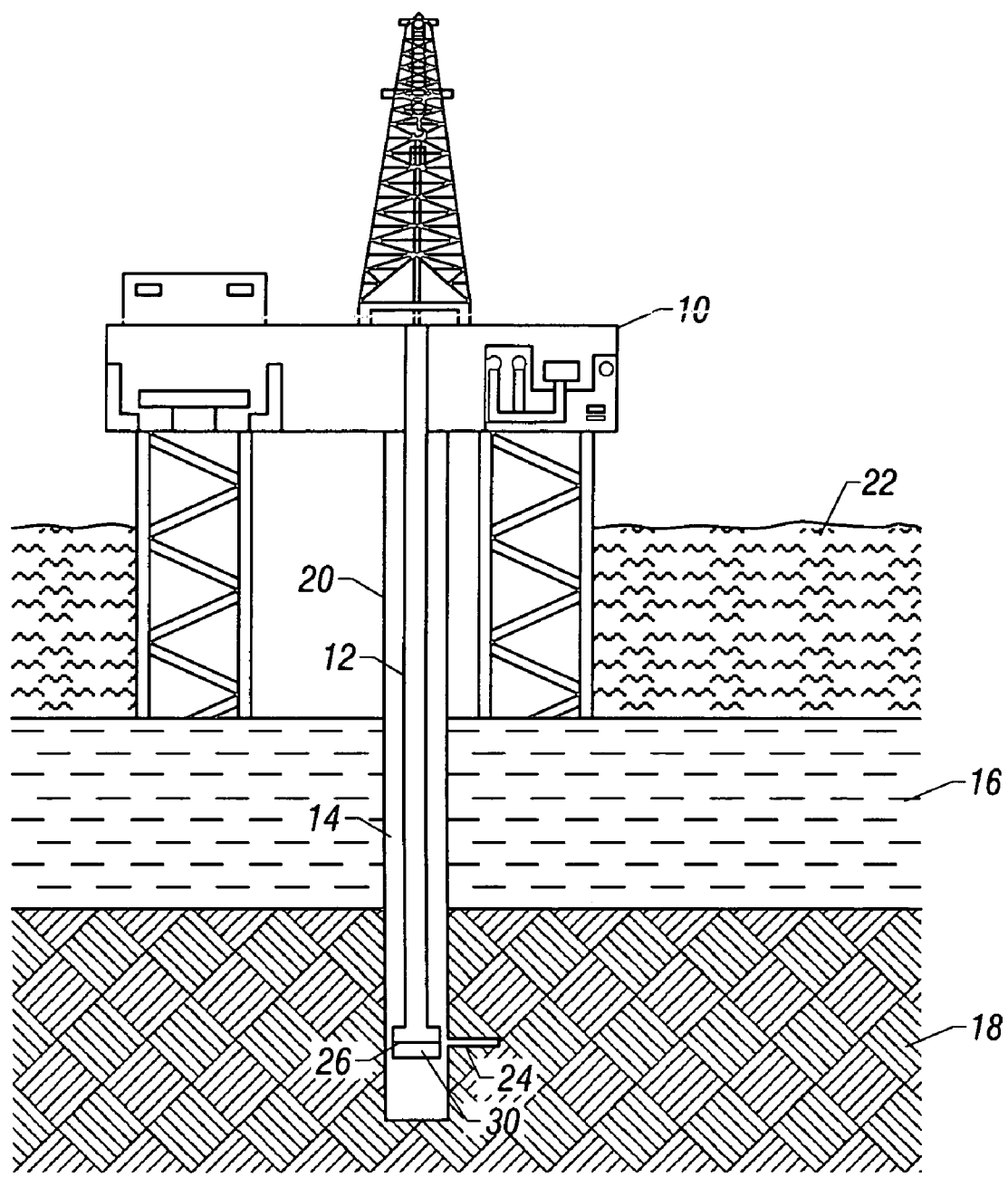

FIG. 9 illustrates a representative drilling/production platform 10 having a tubular string 12 extending into a wellbore 14 and incorporating an embodiment of the present invention. The wellbore 14 has penetrated subterranean formations 16, and intersects a productive reservoir 18. A casing string 20 lines the well and provides support and isolation of the wellbore 14 from the reservoir 18, other formations 16 and bodies of water 22. A perforation 24 is created that extends through the casing string 20 and into the productive reservoir 18.

A downhole tool 26 can be inserted into the wellbore 14 by the tubular string or by other means, such as a wireline, drill pipe or slickline. The downhole tool 26 comprises a formation testing tool capable of collecting one or more samples of formation fluid, such as, for example, the MDT formation testing tool. In addition to obtaining a sample of the formation fluid coming from the perforation 24, the downhole tool 26 may also collect data such as temperature and pressure readings.

A hydrogen sulfide testing cell 30 is coupled at an end of the downhole tool 26. A resistivity cell is typically provided in the downhole tool 26. One embodiment of the invention involves removing (and replacing) the resistivity cell with the testing cell 30, since it has little use in wells drilled with oil based mud, or if an optical fluid analyzer is run. Embodiments of the present invention can be inserted into the well on a tubular string, wireline, slickline, as part of the drilling or completion string, or by other methods known to a person of ordinary skill in the art.

Figure 10:
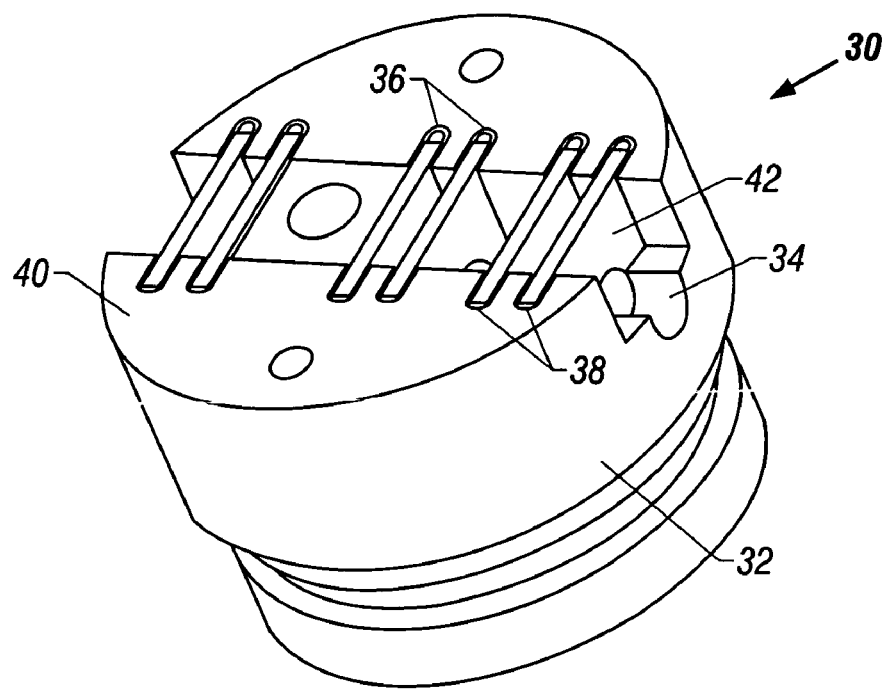

Referring now to FIG. 10, a detailed view of the testing cell 30 of FIG. 9 representing an embodiment of a hydrogen sulfide testing tool is depicted. The cell 30 consists of a housing 32 formed from a modified resistivity cell adapted for use with a downhole tool, such as the MDT tool of FIG. 9. The housing 32 has a fluid flow path 34 passing through it. In the present embodiment, multiple slots 36 intersect the flow path 34. Multiple pairs of metal coupons 38 are inserted into the slots 36. Formation fluid contacts at least a portion of the coupons 38 as it passes through the fluid flow path 34, as well as on the top-surface 40 of the housing. Hydrogen sulfide detection tape 42 may also be inserted in the housing 32 to react with any hydrogen sulfide in much the same manner as the coupons 38. Varying numbers of coupons and/or tape can vary from one to however many can be located within the cell or group of cells. The coupons can be of various shapes and sizes and can be made of any material that is reactive to the presence of hydrogen sulfide.

Figure 11:
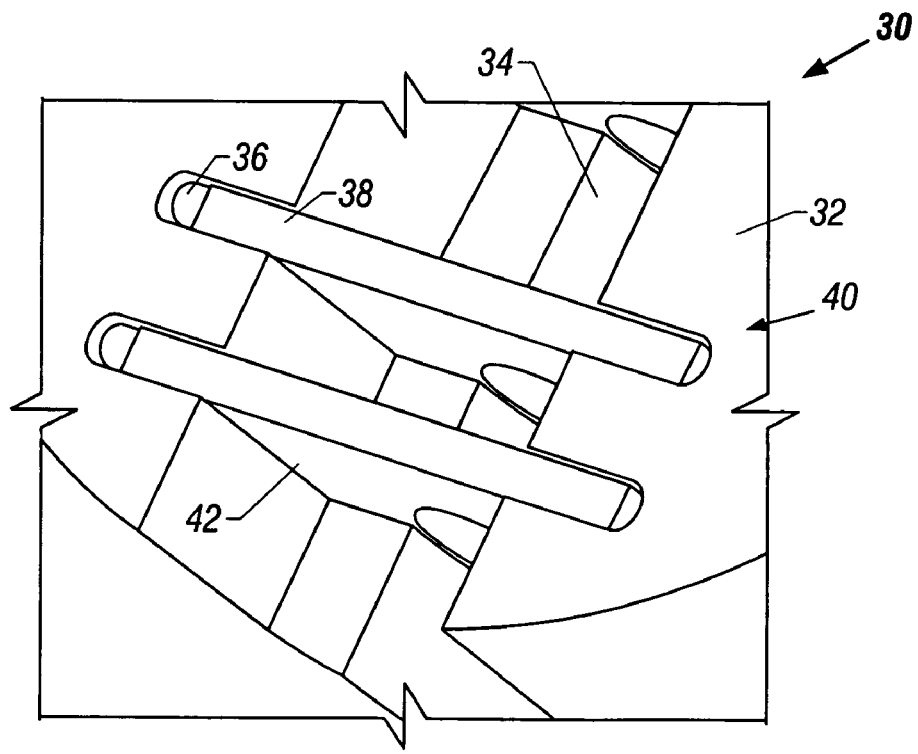

FIG. 11 shows the testing cell 30 of FIG. 10 in greater detail. This illustration zooms in on the hydrogen sulfide tape 42 and coupons 38 as they are positioned in the housing 32. The metal coupons 38 of this embodiment comprise MONEL® and two types of Cupro-nickel. Coupon dimensions of this particular embodiment are approximately 0.062" thick×0.5"×0.8" with a 0.234" diameter hole. Dimensions of the tape are similar; approximately 0.004" thick× 0.5"×1.0" with a 0.250" hole. Other dimensions, shapes and configurations may be envisioned. The tape 42 and coupons 38 can be inserted/removed from the slots 36 in the housing 32 through the use of needle nose pliers or by other means.

When the cell 30 comes out of the hole, a cap is manually removed and the coupons can be visually inspected. If the coupons look the way they did going into the hole, it may be concluded that there was no $H_2S$ is present in any of the fluids that passed through the tool. If any one of the coupons is altered, for example by appearance or color, it is an indication that $H_2S$ is present. As will be depicted more fully below, the changes in the appearance of the coupons may indicate the presence and/or concentration of hydrogen sulfide. Knowing the exposure time to fluid, temperature and pressure, the estimates of the concentration of $H_2S$ can be made. By using coupons with predictable reactions, the presence and/or concentrations of hydrogen sulfide may be detected. Such metals and their reactions are described more fully below. Visual inspection of the coupons is only one method of detection of a reaction to hydrogen sulfide. Alternative means may be provided for detecting a reaction as will be described more fully below.

FIG. 12 illustrates a further embodiment in which an apparatus 70 is used in combination with a downhole sampling and/or testing tool. The apparatus 70 comprises a body 72 having a fluid flow path 74 therethrough, and a plurality of slots 76 in which a coupon 78 is inserted. The fluid flow path 74 enables formation fluid to pass through the apparatus 70 and come in contact with the coupons 78. The apparatus 70 may be positioned in fluid communication with the formation fluid flowing from a sampling/testing probe. The apparatus 70 may be inserted into the probe, a flow line, a sampling chamber, or other parts of the downhole tool. A temperature sensor 80 may be included for temperature measurements and signal transmission.

As shown in greater detail in FIG. 13, coupon 78 may comprise a U-shaped slab that when inserted into the slots 76 exposes one portion 82 of the coupon 78 to the formation fluid while another portion 84 is isolated from the formation fluid. A top surface 86 of the coupon 78 can be coated with a non-reactive substance such as TEFLON® or certain plastics. This surface 86 can provide another area of the coupon 78 that is protected from hydrogen sulfide contact and serve as an unreacted surface for interpretation purposes. The apparatus 70 can comprise material that is non-reactive to hydrogen sulfide.

FIGS. 14 and 15 show an alternate embodiment in which a cell 90 comprises a channel 92 for fluid flow. Within the channel 92 are coupons 94 and a temperature sensor 96. The cell 90 can comprise material that is non-reactive to hydrogen sulfide. In this and other embodiments of the present invention, a sensor 98, can be incorporated within the cell, the sensor having the capability of detecting a reaction to the surface of the sample of material, such as an optical reaction to hydrogen sulfide. The sensor 98 can enable the detection and/or quantification of hydrogen sulfide, without the requirement of removing the tool from the wellbore. The sensor 98 may also comprise a means of transmitting a signal to the surface, for example, an electrical signal sent through a wireline, an optical signal sent through a fiber optic cable, or a pressure pulse signal sent through the wellbore fluid. Detection of reactions may be performed uphole, downhole and/or during operation using visual, sensors or otherwise.

"Coupons" as used herein refers to a detector for identifying and/or measuring hydrogen sulfide. For example, a coupon may be a sample of metal that does not react, unless exposed to $H_2S$. Potential metals may include: Monel® alloy 400 (UNS N04400), 70-30 cupronickel (UNS C71500), 90-10 cupronickel (UNS C70600) as well as others reactive to hydrogen sulfide. It is desirable that the coupon materials that are used cover a range of hydrogen sulfide reactivity, so that a quantitative determination of the hydrogen sulfide content can be made. For example, if one coupon reacts at very low levels of hydrogen sulfide (<5 ppm), a second coupon reacts between approximately 15–25 ppm hydrogen sulfide, and a third coupon reacts between approximately 25–100 ppm. With this type of apparatus the presence of hydrogen sulfide can be observed and a quantitative analysis of the hydrogen sulfide content can be obtained based on an optical change of the surface of the coupon. The term "optically reactive" within the present application means a material having an external surface that changes color in the presence of hydrogen sulfide.

Certain coupons are commercially available from resources, such as Metal Samples/Cortest Instrument Systems, a Division of Alabama Specialty Products, Inc. located at 152 Metal Samples Rd., Munford, Ala. 36268. It is desirable to select coupons adapted to detect hydrogen sulfide in wellbore operations.

Studies were performed to select metals capable of eliciting a detectable response under wellbore conditions. As shown in FIG. 16, several materials were selected for detection of hydrogen sulfide. These materials include: three copper nickel alloys—MONEL® alloy 400, 70-20 cupronickel, and 90-10 cupronickel; three iron-chromium alloys—5Cr, 9Cr and 12Cr steels; 316 stainless steel; Nickel alloy 200, INCOLOY® alloy 600 and alloy B (a nickel/molybdenum alloy).

Tests were conducted in simulated service environments containing low to moderate concentrations of hydrogen sulfide (nominally 5 to 100 ppm $H_2S$ in nitrogen). At a test pressure of approximately 1000 psi, these environments were intended to simulate a well bore environment with a hydrogen sulfide partial pressure of 0.005 to 0.10 psia. Tests were conducted in the temperature range of approximately 250–400° F., which was presumed to be a reasonable range of service temperature for downhole tools, in this case. The test pressure for all tests was approximately 1000 psi. The exposures were achieved by charging an autoclave with a certain level of hydrogen sulfide attained through purging with a pre-mixed hydrogen sulfide/nitrogen test gas. The materials, specimens, test procedures and test results are discussed in detail in the following sections.

The exposure tests were conducted in a 0.5 liter alloy C-276 test vessel with external heaters with the mixed hydrogen sulfide/nitrogen test gas at test temperatures ranging from approximately 250–400° F. The test pressure for these tests was approximately 1000 psi. The duration of these tests was between 2–6 hours. With the exception of the first two tests in Phase I, all tests in both the Phase I and Phase II programs included distilled water as the liquid phase. The first two tests used oil mud as the liquid phase.

The test procedure involved heating of the test vessel to the test temperature and purging the contents of the test vessel with a hydrogen sulfide/nitrogen mixed gas until the outlet concentration of hydrogen sulfide reached the desired level. At this point, the valves to the test vessel were closed and gas samples were taken periodically from the vessel.

The tests were performed in two phases. The initial part of Phase I involved exposure of three coupons—MONEL® alloy 400, 70-30 cupronickel and 90-10 cupronickel. However, the final three tests also contained Nickel alloy 200 and alloy B. Phase II involved the exposure to the three iron-chromium alloys, 316 stainless steel, INCOLOY® alloy 600 and alloy B. Specimen evaluation was performed by visual examination. The presence and coloration of the corrosion product on the various corrosion coupons was determined.

The results of the coupon tests conducted in the Phase I and Phase II programs are summarized in FIGS. 17 and 18 respectively. The first two tests conduct with oil-based mud as the liquid phase were used to examine the influence of oil-based mud on the corrosion of the alloys without the presence of hydrogen sulfide. As indicated in FIG. 17, only a slight tarnishing of the surface was observed to occur in the cupronickel alloy coupon over the range of temperatures from 250–400° F. for durations of 2–6 hours. This type of attack was characterized as a light darkening of the specimen surfaces. For the MONEL® and 70/30 cupronickel, this observation was manifested by a thin, light-gray surface layer. For the 90-10 cupronickel, this was a darkening of the natural light orange color of this alloy. No attack was found on the MONEL® alloy 400 coupon in these first two tests. The tarnish film observed in these studies was described as allowing the metallic nature of the coupon to be observed.

Tests 3, 5, 7 and 9 were conducted in a distilled water environment saturated with nitrogen gas (without hydrogen sulfide) at test temperatures of 250, 300, 350 and 400° F. These exposures produced only a slight tarnish film as evidenced by a darkening of the natural coloration of the coupon while retaining the metallic quality of the coupon.

Tests 4, 6, 8 and 10 were conducted in a distilled water environment saturated with an hydrogen sulfide/nitrogen gas mixture. Following these exposures, coupons of the three copper-containing alloys were corroded producing a dull, gray to dark gray surface film. These films did not have the metallic luster of tarnished or as-received specimens. Tests 11 through 15 were conducted at lower levels of hydrogen sulfide (25 ppm, 10 ppm and 5 ppm) for periods of 2–6 hours. Whereas the coupons from these tests varied in coloration and in degree of film formation, all exposures produced corroded surfaces on the coupons that were characterized as being dull gray to dark gray in color.

Following the completion of the above-mentioned Phase I tests, three more tests were conducted that included additional alloys with the aim to find materials which would show a color transformation at higher hydrogen sulfide concentrations than observed for the nickel-copper alloys. Tests 16 through 18 examined the behavior of Nickel alloy 200, alloy B and INCOLOY® alloy 600 at intermediate hydrogen sulfide levels (e.g., 10–25 ppm). The results in Table 2 indicate that Nickel 200 exhibited a light gray corrosion film at 25 ppm hydrogen sulfide but not at 10 ppm and 18 ppm. By comparison, alloy B showed a transformation from a tarnish film at 10 ppm to a gray corrosion film at 18 ppm that darkened when going to 25 ppm hydrogen sulfide. INCOLOY® 600 had a tarnish film in all three tests and did not exhibit a transformation to a corrosion film at up to 25 ppm concentration.

Based on the results of the tests in Phase I depicted in FIG. 17, it appears that all three copper-containing alloys (MONEL® alloy 400, 70/30 cupronickel and 90/10 cupronickel) produced a discernable color change at very low levels of hydrogen sulfide (<5 ppm). Furthermore, it was observed that alloy B produced a noticeable color change between 18 and 25 ppm hydrogen sulfide. Therefore, the next step in this exploratory study was to try to find a material that would indicate the presence of higher levels of hydrogen sulfide in the range of 25–100 ppm. A search for new candidate materials was conducted and a test matrix developed. The list of candidate materials developed included INCOLOY® alloy 600, three iron-chromium alloys (5Cr, 9Cr and 12Cr) and 316 stainless steel. Alloy B and Nickel alloy 200 were also included in the program for comparison.

Results indicate that the iron-chromium alloys and 316 stainless steel do not show a distinct transition in the appearance of their corrosion films over the range 25 to 100 ppm hydrogen sulfide at either 250 or 300° F. However, the surface films for all of the iron-chromium alloys exhibit a color change from gray to dark gray over this broad range of concentration and test temperature. The 316 stainless steel also made a change from tarnish film to light gray in this range, as well.

The corrosion films produced on Nickel alloy 200 start to form in the range of approximately 25 ppm hydrogen sulfide, but vary in coloration from dark gray to lighter gray with concentration up to approximately 100 ppm. Therefore, a consistent and easily discernable color change was not produced.

As observed in Phase I, INCOLOY® alloy 600 produced only light tarnish films up to approximately 25 ppm hydrogen sulfide. The Phase II tests showed that the corrosion films changed from gray to black over the range of about 25 to 100 ppm, which was particularly noticeable by visual examination between about 75 to 100 ppm at 250° F. and at 50 ppm at 300° F.

The initial phase of testing in this program revealed that all of the copper-containing alloys (MONEL® alloy 400 and the two cupronickels) examined were very sensitive to color change when exposed to hydrogen sulfide at elevated temperatures. The lowest concentration of hydrogen sulfide used for testing (5 ppm) produced clear signs of a gray to dark gray corrosion product on each of these materials. In terms of partial pressure, this condition was 0.005 psia hydrogen sulfide (5 ppm×1000 psi). It was also assessed that this process was not highly dependent on test temperature. Therefore, any of the three copper-containing materials should be adequate for identifying service conditions with only traces of hydrogen sulfide.

The Phase I program also identified candidate materials for use in assessing higher levels of hydrogen sulfide in service environments. These included alloy B and INCOLOY® alloy 600. The Phase I tests showed that alloy B produced a corrosion product color change to dark gray between about 18–25 ppm. The partial pressure equivalents for these conditions are 0.018 to 0.025 psia hydrogen sulfide.

The results of the Phase II program, shown in FIG. 18, indicated that INCOLOY® alloy 600 produced a corrosion product color change between about 50 ppm and 75 ppm depending on the service temperature in the range of 250–300° F. The partial pressure equivalent of these conditions are 0.050 to 0.1 psia hydrogen sulfide.

The results of these tests imply that a simple corrosion coupon may provide a semi-quantitative method for assessing the hydrogen sulfide level in service environment. These results also indicate that oil mud of the type supplied for evaluation in this study do not complicate the results by producing false positive indications for hydrogen sulfide. It should be realized that other factors common to field operations might complicate direct application of these results. The first and most important factor is temperature. In this study it was also observed that changes in temperature might produce lighter or darker film coloration. Secondly, time of exposure may also produce similar changes. However, in the limited time study conducted in this program, no major influence was found. Other factors that could influence the application of these results include presence of persistent oil films or inhibitive chemicals in the production environment that could act as a barrier to corrosion of the metal surface.

Figure 19A:
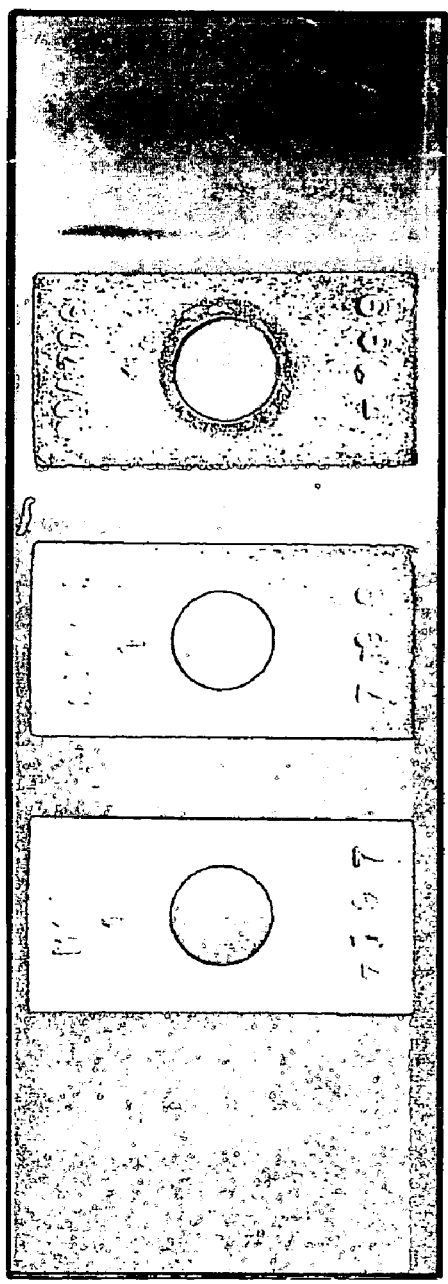
Figure 19B:
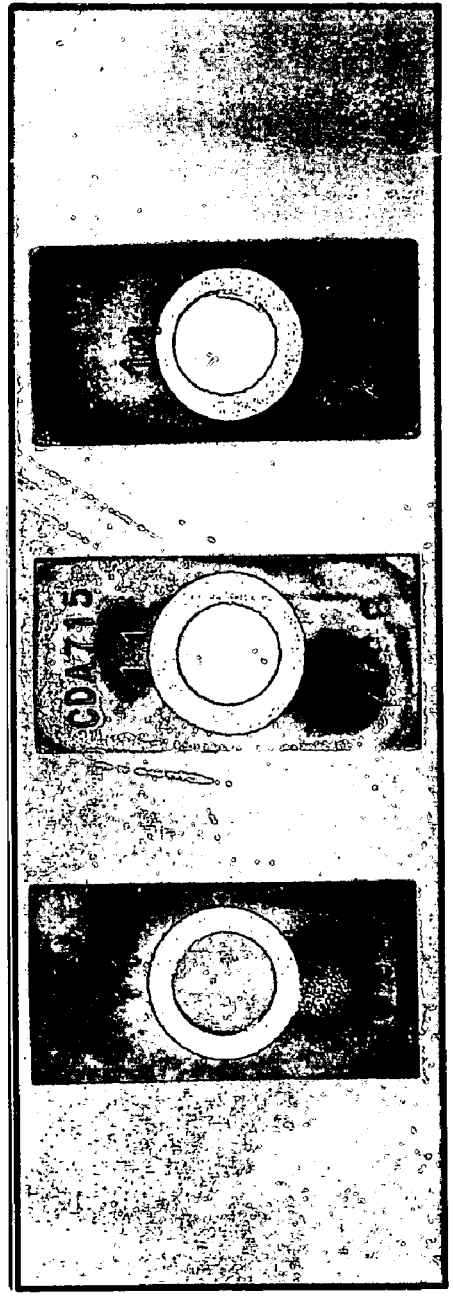
Figure 20A:
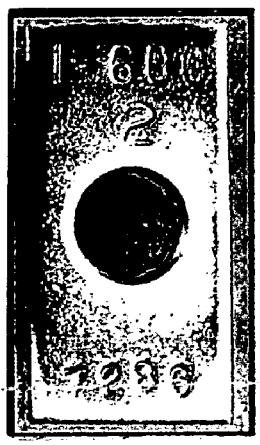
Figure 20D:
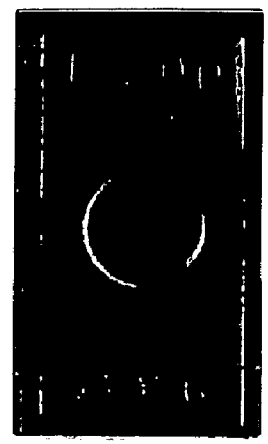
Figure 20B:
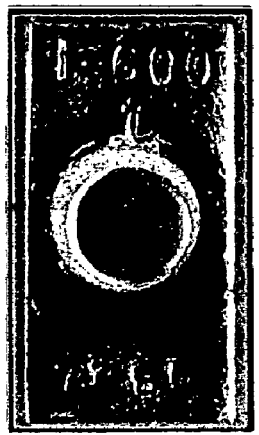
Figure 20E:
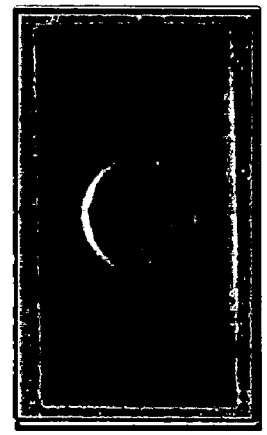
Figure 20C:
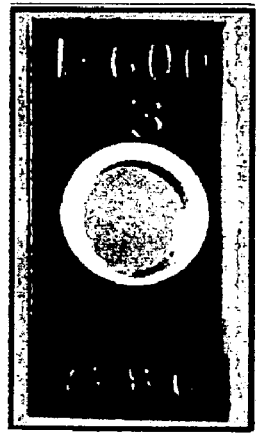
Figure 21A:
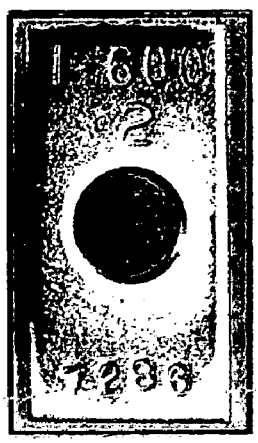
Figure 21D:
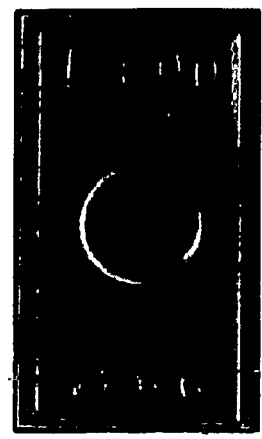
Figure 21B:
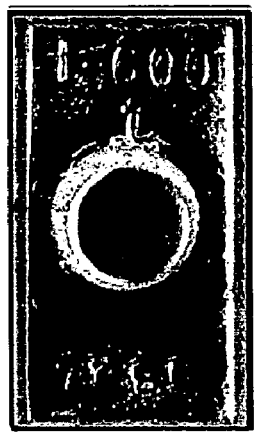
Figure 21E:
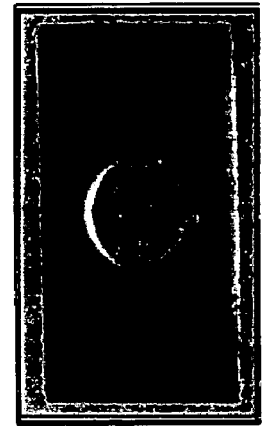
Figure 21C:
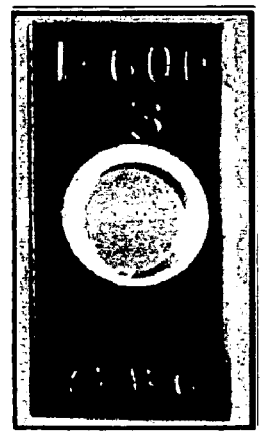
Figure 22A:
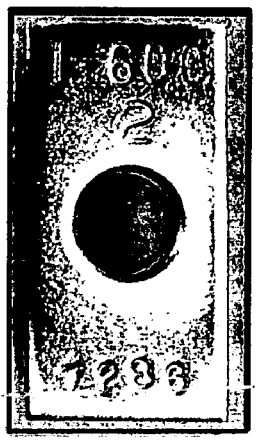
Figure 22D:
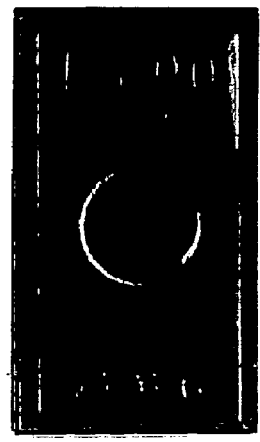
Figure 22B:
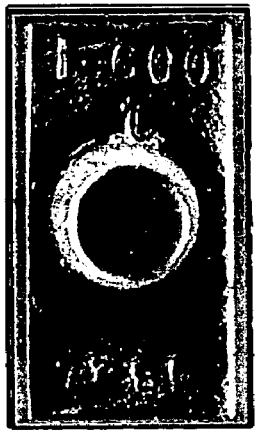
Figure 22E:
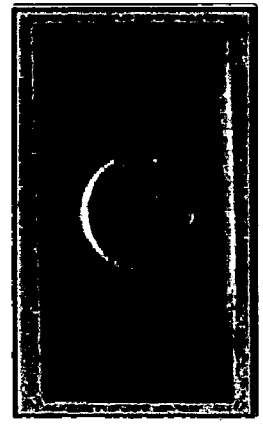
Figure 22C:
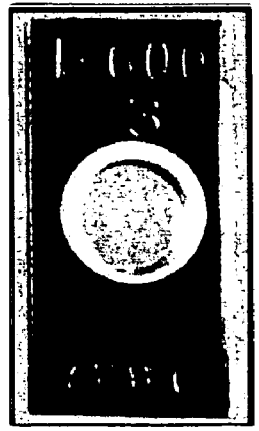

FIGS. 19 through 22 depict coupons made of various materials after being exposed to differing concentrations of hydrogen sulfide. The visual changes provide a means for detection of hydrogen sulfide and its concentration. These illustrate the reaction of the coupons at increased hydrogen sulfide concentration. FIG. 19A depicts three copper containing specimens with tarnish films from exposure. The surface darkens while retaining shiny metallic luster. FIG. 19 shows examples of gray-black corrosion films on copper containing alloys. The metal has dark surface films with no metallic luster.

FIGS. 20 A–E show the change in corrosion films on MONEL® with increasing levels of hydrogen sulfide in the environment. FIG. 20A shows an exposure to 0 ppm hydrogen sulfide, FIG. 20B shows an exposure to 5 ppm hydrogen sulfide, FIG. 20C shows an exposure to 10 ppm hydrogen sulfide, FIG. 20D shows an exposure to 25 ppm hydrogen sulfide and FIG. 20E shows an exposure to 50 ppm hydrogen sulfide. The change in coloration from tarnish to dark gray appears between 5 and 10 ppm hydrogen sulfide.

As will be readily apparent to those skilled in the art, the present invention may easily be produced in other specific forms without departing from its spirit or essential characteristics. The disclosed embodiments are, therefore, to be considered as merely illustrative and not restrictive. The scope of the invention is indicated by the claims that follow rather than the foregoing description, and all changes which come within the meaning and range of equivalence of the claims are therefore intended to be embraced therein.

What is claimed is:

1. A method of identifying the presence of hydrogen sulfide in a wellbore penetrating a subterranean formation, comprising:
   lowering a formation evaluation tool comprising at least one coupon operatively connected thereto into the wellbore such that the coupon is exposed to fluid in the wellbore, the at least one coupon being optically reactive to the presence of hydrogen sulfide; drawing formation fluid samples from the subterranean formation into the formation evaluation tool;
   determining whether an optical reaction has occurred to the at least one coupon.

2. The method of claim 1, further comprising:
   inspecting the at least one coupon at the surface for an optical reaction.

3. The method of claim 1, further comprising:
   inspecting the optical reaction of the at least one coupon to estimate the quantity of hydrogen sulfide contained in the fluid.

4. The method of claim 1, further comprising: retrieving the tool from the wellbore.

5. The method of claim 1, further comprising:
   taking temperature readings of the reservoir fluid.

6. The method of claim 1, further comprising:
   taking temperature readings of the reservoir fluid;
   inspecting the at least one coupon for exposure to hydrogen sulfide; and
   estimating the hydrogen sulfide content of the reservoir fluid based upon the inspection of the optical reaction of the at least one coupon and the temperature readings of the reservoir fluid.

7. The method of claim 1, wherein the at least one coupon is selected from a group comprising chromium, nickel and steel alloys.

8. The method of claim 1, further comprising:
   detecting an optical reaction of the at least one coupon with a sensor.

9. The method of claim 8, further comprising:
   transmitting a signal indicating an optical reaction of the at least one coupon.

10. A method for identifying the presence of hydrogen sulfide in a subsurface formation penetrated by a wellbore, comprising:
    lowering a formation evaluation tool into the wellbore, the tool comprising a housing, at least one coupon with a surface that is optically reactive to the presence of hydrogen sulfide, and at least one passage for conducting formation fluid to coupon drawing formation fluid samples from the subterranean formation into the formation evaluation tool;
    delivering formation fluid to coupon via the passage;
    retrieving the formation evaluation tool from the wellbore; and
    inspecting the coupon for an optical reaction.

11. The method of claim 10, wherein the at least one coupon is selected from a group comprising chromium, nickel and steel alloys.

12. The method of claim 10, wherein the tool comprises a plurality of of at least one coupons, the coupon capable of different optical reactions in response to varying hydrogen sulfide concentrations.

13. The method of claim 10, further comprising:
    taking temperature readings of the formation fluid;
    inspecting the optical reaction of the at least one coupon to determine if hydrogen sulfide is present; and
    estimating the hydrogen sulfide content of the fluid utilizing the optical reaction on the surface of the at least one coupon and the temperature readings of the formation fluid.

14. The method of claim 10, further comprising:
    transporting formation fluid through the formation evaluation tool; and
    collecting formation fluid samples within the formation evaluation tool.

15. A method for identifying the presence of hydrogen sulfide in a subsurface formations penetrated by a wellbore, comprising the steps of:
    lowering a formation evaluation tool into the wellbore, the tool including a housing having at least one coupon that is reactive to the presence of hydrogen sulfide and a passage for conducting formation fluid to coupon drawing formation fluid samples from the subterranean formation into the formation evaluation tool delivering formation fluid to coupon via the passages;
    retrieving the formation evaluation tool from the wellbore; and
    inspecting coupon for an optical reaction.

16. The method of claim 15, wherein the coupon is a metal.

17. The method of claim 16, wherein the metal is selected from a group comprising copper and nickel alloys.

18. The method of claim 15 wherein the coupon reacts to hydrogen sulfide by changing color.

19. A method of reservoir analysis, comprising:
    lowering a formation evaluation tool into a wellbore that penetrates a reservoir, the formation evaluation tool comprising at least one coupon that is optically reactive to the presence of hydrogen sulfide;
    flowing formation fluid through the formation evaluation tool;
    exposing the at least one coupon to formation fluid upon the formation fluid entry into the wellbore;
    taking temperature readings of the formation fluid;
    collecting formation fluid samples within the formation evaluation tool;
    retrieving the formation evaluation tool from the wellbore;
    inspecting the at least one coupon for an optical reaction; and
    estimating the hydrogen sulfide content of the formation fluid within the reservoir utilizing the inspection of the optical reaction of the at least one coupon and the temperature readings of the formation fluid.

20. A formation evaluation tool for drawing fluid from a subterranean formation therein, comprising:
    a housing; and
    at least one coupon operatively connected to the housing, the at least one coupon being optically reactive to the presence of hydrogen sulfide positioned in the housing;
    wherein the at least one coupon is adapted to be exposed to reservoir fluid upon the reservoir fluid entry into the apparatus.

21. The formation evaluation tool of claim 20, wherein the coupon is a metal.

22. The formation evaluation tool of claim 21, wherein the metal is selected from a group comprising comprising chromium, nickel and steel alloys.

23. The formation evaluation tool of claim 20, wherein the coupon reacts to hydrogen sulfide by changing color.

24. The formation evaluation tool of claim 20, further comprising a temperature sensor.

25. The formation evaluation tool of claim 20, further comprising a pressure sensor.

26. The formation evaluation tool of claim 20, wherein the at least one coupon comprises removable coupons having different reactive responses to hydrogen sulfide.

27. The formation evaluation tool of claim 20, wherein the housing further comprises a coupon holder that is resistant to hydrogen sulfide, the housing capable of retaining the at least one coupon.

28. The formation evaluation tool of claim 20, wherein the apparatus comprises at least three hydrogen sulfide detection coupons.

29. The formation evaluation tool of claim 20, wherein the apparatus further comprises a sensor capable of detecting a an optical reaction in the at least one coupon.

30. The formation evaluation tool of claim 29, wherein the sensor is capable of transmitting a signal indicating an optical reaction in the at least one coupon.

31. A formation evaluation tool for drawing fluid from a subterranean formation therein, comprising:
 a plurality of coupons that are optically reactive to the presence of hydrogen sulfide;
 a housing capable of retaining the coupons and having a passage for communicating formation fluids between a wellbore and the coupons;
 a temperature sensor;
 a probe capable of flowing formation fluids into the formation evaluation tool;
 wherein when the formation fluids are pumped through the formation evaluation tool the coupons are exposed to the formation fluid upon the formation fluid entry into the formation evaluation tool; and
 wherein the surface of the plurality of coupons are capable of changing color upon contact with hydrogen sulfide and can be interpreted to determine the hydrogen sulfide content in the formation fluids.

32. The formation evaluation tool of claim 31, wherein the formation evaluation tool further comprises a sensor capable of detecting an optically reaction in the at least one coupon as a result of detecting hydrogen sulfide.

33. The formation evaluation tool of claim 32, wherein the sensor is capable of transmitting a signal indicating an optically reaction in the at least one coupon as a result of detecting hydrogen sulfide.

34. An apparatus for identifying the presence of hydrogen sulfide in a wellbore penetrating a subsurface formation, comprising:
 a formation evaluation tool capable of drawing fluid from the subsurface formation therein including a housing having at least one coupon that is reactive to the presence of hydrogen sulfide, the housing having a passage for conducting formation fluid to the coupon when the formation evaluation tool is lowered into the wellbore.

35. The apparatus of claim 34, wherein the coupon is a metal.

36. The apparatus of claim 35, wherein the metal is selected from a group comprising copper and nickel alloys.

37. The apparatus of claim 34 wherein the coupon reacts to hydrogen sulfide by changing color.

* * * * *